(12) United States Patent
Ikeda et al.

(10) Patent No.: US 8,759,590 B2
(45) Date of Patent: Jun. 24, 2014

(54) INDENOPYRENE COMPOUND, ORGANIC THIN FILM SOLAR CELL MATERIAL USING THE SAME, AND ORGANIC THIN FILM SOLAR CELL

(75) Inventors: Hidetsugu Ikeda, Chiba (JP); Ryoji Maeda, Chiba (JP); Masahide Matsuura, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 309 days.

(21) Appl. No.: 13/056,777

(22) PCT Filed: Oct. 4, 2009

(86) PCT No.: PCT/JP2009/057389
§ 371 (c)(1),
(2), (4) Date: May 2, 2011

(87) PCT Pub. No.: WO2010/013520
PCT Pub. Date: Feb. 4, 2010

(65) Prior Publication Data
US 2011/0240125 A1  Oct. 6, 2011

(30) Foreign Application Priority Data
Jul. 30, 2008  (JP) ................................. 2008-196273

(51) Int. Cl.
*C07C 211/00* (2006.01)
(52) U.S. Cl.
USPC ........................................ 564/426
(58) Field of Classification Search
None
See application file for complete search history.

(56) References Cited

U.S. PATENT DOCUMENTS

| | | | |
|---|---|---|---|
| 6,815,090 B1 | 11/2004 | Tagami et al. | |
| 6,818,327 B2 | 11/2004 | Tagami et al. | |
| 2003/0054200 A1 | 3/2003 | Tagami et al. | |
| 2004/0214043 A1 | 10/2004 | Tagami et al. | |
| 2005/0212409 A1* | 9/2005 | Shi et al. | 313/504 |
| 2006/0024523 A1 | 2/2006 | Tagami et al. | |
| 2006/0194074 A1 | 8/2006 | Funahashi | |
| 2007/0003788 A1 | 1/2007 | Tagami et al. | |
| 2007/0292714 A1 | 12/2007 | Funahashi | |
| 2008/0074045 A1 | 3/2008 | Tagami et al. | |

FOREIGN PATENT DOCUMENTS

| | | |
|---|---|---|
| WO | WO 01/23497 A1 | 4/2001 |
| WO | WO 2006/030527 A1 | 3/2006 |
| WO | WO 2006/082705 A1 | 8/2006 |

OTHER PUBLICATIONS

International Search Report of PCT/JP2009/057389, Date of completion May 11, 2009, Date of Mailing May 19, 2009, Japanese Patent Office.
Masahiro Minabe, Norio Shibuya, Nitration of Indeno[1,2,3-cd] pyrene and Mutagenic Activities of Related Compounds, Chemical Research in Toxicology, 1989, vol. 2, No. 6, p. 357-358.
Abstract: Hioki Takanori et al., "Photoelectric Converting Film, and Solar Battery Photoelectric Converting Element, or Imaging Element Including Same", Date of publication of application Dec. 27, 2007, Publication No. 2007-335760.
Abstract: Toma Tetsuya et al., Organic Thin-Film Solar Cell, Date of publication of application : Feb. 14, 2008, Publication No. 2008-034764.
Abstract: Shirakawa Makoto, "Organic Photoelectric Conversion Element", Date of publication of application : Apr. 17, 2008, Publication No. 2008-091380.

* cited by examiner

*Primary Examiner* — Clinton Brooks
(74) *Attorney, Agent, or Firm* — Millen, White, Zelano & Branigan, P.C.

(57) ABSTRACT

A specified indenopyrene compound containing a disubstituted amino group substituted with a group having a carbon number of from 1 to 40, which is a useful indenopyrene compound as an organic electronics material, and in particular, an indenopyrene compound which when used for organic thin film solar cells, displays a photoelectric conversion characteristic with high efficiency, is provided.

9 Claims, No Drawings

INDENOPYRENE COMPOUND, ORGANIC THIN FILM SOLAR CELL MATERIAL USING THE SAME, AND ORGANIC THIN FILM SOLAR CELL

TECHNICAL FIELD

The present invention relates to an indenopyrene compound and an organic thin film solar cell material using the same, and further to an organic thin film solar cell using the subject organic thin film solar cell material.

BACKGROUND ART

Similar to photodiodes or imaging devices that convert optical signals into electrical signals, solar cells are an apparatus that displays an electrical output against an optical input and are an apparatus that displays a reverse response to that of electroluminescence (EL) devices that display an optical output against an electrical input. In recent years, such a solar cell has been being greatly watched as a clean energy source against the background of a fossil fuel depletion problem or a global warming problem, and research and development have been keenly carried out. Though silicon based solar cells using monocrystalline silicon, polycrystalline silicon, amorphous silicon or the like have been put into practical use so far, in view of the facts that the silicon based solar cells are expensive and that a shortage problem of raw material silicon or the like has become an issue, a demand for the development of a next-generation solar cell is increasing. Under such a background, an organic thin film solar cell which is inexpensive, low in toxicity and free from concern of a shortage of raw material greatly gets attention as a next-generation solar cell following the silicon based solar cell.

At the beginning, the research on the organic thin film solar cell was advanced on the basis of a single layer film using a merocyanine dye or the like. However, as a result of further research and development, it was found that a conversion efficiency (photoelectric conversion efficiency) from an optical input to an electrical output is enhanced by using a multilayered film having an "n-layer" that transports an electron and a "p-layer" that transports a hole, and since then, the multilayered film has become the main current. Materials used at the beginning of studying the multilayered film were copper phthalocyanine (CuPc) for the p-layer and a peryleneimide (e.g., PTCBI) for the n-layer, respectively. Thereafter, though it was found the photoelectric conversion efficiency is enhanced by inserting an "i-layer (mixed layer made of a p-material and an n-material)" between the p-layer and the n-layer to increase the lamination, the same materials were still used for the p-layer and the n-layer, respectively.

Thereafter, it was found that the photoelectric conversion efficiency is more enhanced by a stack cell configuration in which several layers of "p-layer/i-layer/n-layer" are repeatedly laminated. Materials used at that time were a phthalocyanine for the p-layer and a fullerene ($C_{60}$) for the n-layer, respectively.

On the other hand, in organic thin film solar cells using a polymer, a research of a so-called bulk heterostructure in which a conductive polymer and a $C_{60}$ derivative are used as a material of the p-layer and a material of the n-layer, respectively, and these materials are mixed and thermally treated to induce micro layer separation, thereby increasing a heterointerface and enhancing the photoelectric conversion efficiency was chiefly carried out. Material systems used herein were chiefly poly-3-hexylthiophene (P3HT) as the material of the p-layer and a $C_{60}$ derivative (PCBM) as the material of the n-layer, respectively.

In the light of the above, in the organic thin film solar cells, the materials of the respective layers have not developed so much from about the beginning, and phthalocyanine derivatives, peryleneimide derivatives and $C_{60}$ derivatives are still used. In consequence, in order to increase the photoelectric conversion efficiency, the development of a new material as a replacement of these conventional materials is earnestly desired.

Now, in general, the operation process of an organic solar cell is composed of an elementary process including (1) light absorption and exciton formation, (2) exciton diffusion, (3) charge separation, (4) carrier transfer and (5) electromotive force generation, and there are generally not many organic materials displaying an absorption characteristic in agreement with a sunlight spectrum. Thus, in many cases, a high photoelectric conversion efficiency could not be achieved. For example, in organic EL devices, the development of which is energetically advanced in recent years, amine compounds which are excellent as a hole injection material as well as a hole transport material have been discovered. However, even when such an amine compound is used as the material of the p-layer for organic thin film solar cell, there is involved such a drawback that the absorption characteristic against the sunlight spectrum is insufficient, so that a sufficient photoelectric conversion efficiency is not obtained.

In general, it is known that in order to bear absorption in a visible light region on an organic compound, it would be good to expand a π-electron conjugated structure to make an absorption maximum wavelength long. However, when the conjugated system is overly expanded to make the molecular weight excessively large, there are encountered such a fault that not only the solubility in a solvent is lowered to make it difficult to achieve purification, but a sublimation temperature rises to make it impossible to achieve sublimation and purification, and so forth. Then, polyacenes have been developed as a material capable of efficiently making the absorption wavelength long while controlling the molecular weight to some extent (see Patent Documents 1 to 3).

PRIOR ART DOCUMENT

Patent Document

[Patent Document 1] JP-A-2007-335760
[Patent Document 2] JP-A-2008-34764
[Patent Document 3] JP-A-2008-91380

SUMMARY OF THE INVENTION

Problem to be Solved by the Invention

However, in the polyacenes described in Patent Documents 1 to 3, if a condensed ring number of the polyacene structural site is increased for the purpose of expanding the visible absorption region, there were involved such problems that because of instability against light or oxygen, purification or handling is difficult; that realization of a high purity is difficult; and that practicality is poor. Also, there was involved such a defect that when such a polyacene is used as an organic solar cell material, its photoelectric conversion efficiency is not sufficient.

Under such circumstances, the present invention has been made, and an object thereof is to provide an indenopyrene compound which is useful as an organic electronics material, and in particular, an indenopyrene compound which when used for organic thin film solar cells, displays a photoelectric conversion characteristic with high efficiency.

Means for Solving the Problem

The present inventors made extensive and intensive investigations. As a result, it has been found that the foregoing object can be achieved by an indenopyrene compound having specified substituents. The present invention has been accomplished on the basis of such knowledge.

That is, the present invention provides:

1. An indenopyrene compound represented by the following general formula (I):

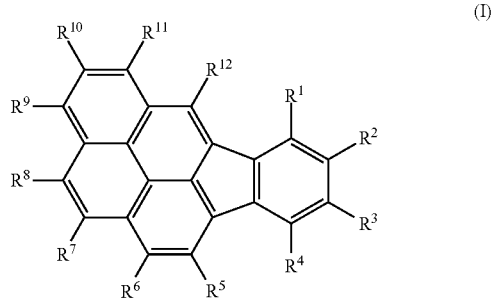

(in the formula, each of $R^1$ to $R^{12}$ independently represents a hydrogen atom or a group selected among a substituted or unsubstituted alkyl group having a carbon number of from 1 to 40, a substituted or unsubstituted aryl group having a carbon number of from 6 to 40, a substituted or unsubstituted heteroaryl group having a carbon number of from 3 to 40, a substituted or unsubstituted alkoxy group having a carbon number of from 1 to 40, a substituted or unsubstituted aryloxy group having a carbon number of from 6 to 40 and a disubstituted amino group substituted with a group having a carbon number of from 1 to 40; $R^6$ and $R^7$ may be bonded to each other to form a ring; and at least one member of $R^1$ to $R^{12}$ is a disubstituted amino group substituted with a group having a carbon number of from 1 to 40);

2. The indenopyrene compound as set forth above in 1, wherein the disubstituted amino group substituted with a group having a carbon number of from 1 to 40 is an amino group represented by the general formula (II):

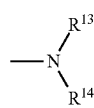

(in the formula, each of $R^{13}$ and $R^{14}$ independently represents a substituted or unsubstituted alkyl group having a carbon number of from 1 to 40 or a substituted or unsubstituted aryl group having a carbon number of from 6 to 40);

3. The indenopyrene compound as set forth above in 1, wherein in the foregoing general formula (I), each of $R^1$ to $R^{12}$ other than a disubstituted amino group substituted with a group having a carbon number of from 1 to 40 is independently a hydrogen atom, a substituted or unsubstituted alkyl group having a carbon number of from 1 to 40 or a substituted or unsubstituted aryl group having a carbon number of from 6 to 40;

4. The indenopyrene compound as set forth above in 1, wherein in the foregoing general formula (I), at least one member selected among $R^2$, $R^3$ and $R^9$ is a disubstituted amino group substituted with a group having a carbon number of from 1 to 40;

5. The indenopyrene compound as set forth above in 2, wherein in the foregoing general formula (I), at least one member selected among $R^2$, $R^3$ and $R^9$ is the disubstituted amino group represented by the general formula (II) and is a disubstituted amino group in which each of $R^{13}$ and $R^{14}$ is independently a substituted or unsubstituted aryl group having a carbon number of from 6 to 40;

6. The indenopyrene compound as set forth above in 4, wherein in the foregoing general formula (I), $R^1$ to $R^{12}$ other than a disubstituted amino group substituted with a group having a carbon number of from 1 to 40 are a hydrogen atom;

7. The indenopyrene compound as set forth above in 5, wherein in the foregoing general formula (I), $R^1$ to $R^{12}$ other than a disubstituted amino group substituted with a group having a carbon number of from 1 to 40 are a hydrogen atom;

8. An organic thin film solar cell material comprising the indenopyrene compound as set forth above in any one of 1 to 7;

9. An organic thin film solar cell having at least a p-layer (hole transport layer) between a pair of electrodes, wherein the subject p-layer contains the organic thin film solar cell material as set forth above in 8; and 10. An apparatus comprising the organic thin film solar cell as set forth above in 9.

Effect of the Invention

According to the present invention, an indenopyrene compound which is useful for organic electronics materials, for example, organic electroluminescence materials, organic semiconductor materials, organic field effect transistor materials, organic solar cell materials, etc., can be obtained. In particular, by using the subject indenopyrene compound for organic thin film solar cell materials, an organic thin film solar cell that displays an energy conversion characteristic with high efficiency is obtained.

MODE FOR CARRYING OUT THE INVENTION

Indenopyrene Compound

The indenopyrene compound of the present invention is represented by the following general formula (I).

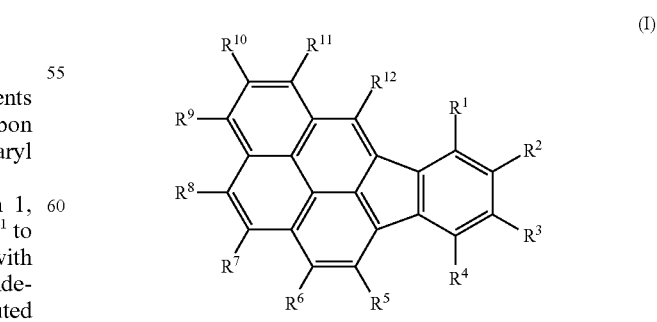

In the formula, each of $R^1$ to $R^{12}$ independently represents a hydrogen atom or a group selected among a substituted or unsubstituted alkyl group having a carbon number of from 1 to 40, a substituted or unsubstituted aryl group having a carbon number of from 6 to 40, a substituted or unsubstituted heteroaryl group having a carbon number of from 3 to 40, a substituted or unsubstituted alkoxy group having a carbon number of from 1 to 40, a substituted or unsubstituted aryloxy group having a carbon number of from 6 to 40 and a disubstituted amino group substituted with a group having a carbon number of from 1 to 40; $R^6$ and $R^7$ may be bonded to each other to form a ring; and at least one member of $R^1$ to $R^{12}$ is a disubstituted amino group substituted with a group having a carbon number of from 1 to 40.

The substituted or unsubstituted alkyl group having a carbon number of from 1 to 40, which is represented by $R^1$ to $R^{12}$, may be straight chain, branched chain or cyclic. Examples of the substituent include halogen atoms such as a fluorine atom, a chlorine atom, a bromine atom, an iodine atom, etc.; a hydroxyl group; alkoxy groups having preferably a carbon number of from 1 to 10 (more preferably a carbon number of from 1 to 5), such as a methoxy group, an ethoxy group, various propoxy groups, various butoxy groups, etc.; aryl groups having preferably a ring-forming carbon number of from 6 to 14, such as a phenyl group, a tolyl group, a naphthyl group, etc.; a cyano group; and so forth.

Specific examples of the subject alkyl group include a methyl group, an ethyl group, a 1-propyl group, a 2-propyl group, a 1-butyl group, a 2-butyl group, a sec-butyl group, a tert-butyl group, a pentyl group, a hexyl group, an octyl group, a decyl group, a dodecyl group, a 2-ethylhexyl group, a 3,7-dimethyloctyl group, a cyclopropyl group, a cyclopentyl group, a cyclohexyl group, a 1-adamantyl group, a 2-adamantyl group, a norbornyl group, a trifluoromethyl group, a trichloromethyl group, a benzyl group, an α,α-dimethylbenzyl group, a 2-phenylethyl group, a 1-phenylethyl group and so forth. Of these, from the viewpoints of easiness of availability of a raw material and the like, alkyl groups having a carbon number of from 1 to 20 are preferable; alkyl groups having a carbon number of from 1 to 6 are more preferable; and a methyl group, an ethyl group, a propyl group, an isopropyl group, a tert-butyl group and a cyclohexyl group are preferable.

In the substituted or unsubstituted aryl group having a carbon number of from 6 to 40, which is represented by $R^1$ to $R^{12}$, examples of the substituent include halogen atoms such as a fluorine atom, a chlorine atom, a bromine atom, an iodine atom, etc.; a hydroxyl group; alkoxy groups having preferably a carbon number of from 1 to 10 (more preferably a carbon number of from 1 to 5), such as a methoxy group, an ethoxy group, various propoxy groups, various butoxy groups, etc.; aryl groups having preferably a ring-forming carbon number of from 6 to 14, such as a phenyl group, a tolyl group, a naphthyl group, etc.; a cyano group; and so forth.

Specific examples of the subject aryl group include a phenyl group, a 2-tolyl group, a 4-tolyl group, a 4-trifluoromethylphenyl group, a 4-methoxyphenyl group, a 4-cyanophenyl group, a 2-biphenylyl group, a 3-biphenylyl group, a 4-biphenylyl group, a terphenylyl group, a 3,5-diphenylphenyl group, a 3,4-diphenylphenyl group, a pentaphenylphenyl group, a 4-(2,2-diphenylvinyl)phenyl group, a 4-(1,2,2-triphenylvinyl)phenyl group, a fluorenyl group, a 1-naphthyl group, a 2-naphthyl group, a 9-anthryl group, a 2-anthryl group, a 9-phenanthryl group, a 1-pyrenyl group, a chrysenyl group, a naphthacenyl group, a choronyl group and so forth. Of these, from the viewpoints of easiness of availability of a raw material and the like, aryl groups having a ring-forming carbon number of from 6 to 18 are preferable; aryl groups having a ring-forming carbon number of from 6 to 14 are more preferable; and a phenyl group, a 4-biphenyl)-group, a 1-naphthyl group, a 2-naphthyl group and a 9-phenanthryl group are still more preferable.

The substituted or unsubstituted heteroaryl group having a carbon number of from 3 to 40, which is represented by $R^1$ to $R^{12}$, may be bonded to any atom if it is at all possible, and for example, in the case of a nitrogen-containing azole based heterocyclic ring, it may be bonded at not only carbon but nitrogen. Examples of the substituent include halogen atoms such as a fluorine atom, a chlorine atom, a bromine atom, an iodine atom, etc.; a hydroxyl group; alkoxy groups having preferably a carbon number of from 1 to 10 (more preferably a carbon number of from 1 to 5), such as a methoxy group, an ethoxy group, various propoxy groups, various butoxy groups, etc.; aryl groups having preferably a carbon number of from 6 to 14, such as a phenyl group, a tolyl group, a naphthyl group, etc.; a cyano group; and so forth.

Specific examples of the subject heteroaryl group include a furanyl group, a thiophenyl group, a pyrrolyl group, an imidazolyl group, a benzimidazolyl group, a pyrazolyl group, a benzopyrazolyl group, a triazolyl group, an oxadiazolyl group, a pyridinyl group, a pyrazinyl group, a triazinyl group, a quinolinyl group, a benzofuranyl group, a dibenzofuranyl group, a benzothiophenyl group, a dibenzothiophenyl group, a carbazolyl group and so forth. Of these, from the viewpoints of easiness of availability of a raw material and the like, heteroaryl groups having a ring-forming atom number of from 6 to 20 are preferable; heteroaryl groups having a ring-forming atom number of from 6 to 14 are more preferable; and a furanyl group, a thiophenyl group, a pyridinyl group and a carbazolyl group are still more preferable.

Examples of the substituted or unsubstituted alkoxy group having a carbon number of from 1 to 40, which is represented by $R^1$ to $R^{12}$, include those in which the alkyl group site thereof is the same as the foregoing alkyl group having a carbon number of from 1 to 40, which is represented by $R^1$ to $R^{12}$. Examples of the substituent include halogen atoms such as a fluorine atom, a chlorine atom, a bromine atom, an iodine atom, etc.; a hydroxyl group; alkoxy groups having preferably a carbon number of from 1 to 10 (more preferably a carbon number of from 1 to 5), such as a methoxy group, an ethoxy group, various propoxy groups, various butoxy groups, etc.; aryl groups having preferably a ring-forming carbon number of from 6 to 14, such as a phenyl group, a tolyl group, a naphthyl group, etc.; a cyano group; and so forth.

Specific examples of the subject alkoxy group include a methoxy group, an ethoxy group, a 1-propyloxy group, a 2-propyloxy group, a 1-butyloxy group, a 2-butyloxy group, a sec-butyloxy group, a tert-butyloxy group, a pentyloxy group, a hexyloxy group, an octyloxy group, a decyloxy group, a dodecyloxy group, a 2-ethylhexyloxy group, a 3,7-dimethyloctyloxy group, a cyclopropyloxy group, a cyclopentyloxy group, a cyclohexyloxy group, a 1-adamantyloxy group, a 2-adamantyloxy group, a norbornyloxy group, a trifluoromethoxy group, a benzyloxy group, an α,α-dimethylbenzyloxy group, a 2-phenylethoxy group, a 1-phenylethoxy group and so forth. Of these, from the viewpoints of easiness of availability of a raw material and the like, alkoxy groups having a carbon number of from 1 to 20 are preferable; alkoxy groups having a carbon number of from 1 to 5 are more preferable; and a methoxy group, an ethoxy group and a tert-butoxy group are still more preferable.

Examples of the substituted or unsubstituted aryloxy group having a carbon number of from 6 to 40, which is represented by $R^1$ to $R^{12}$, include those in which the aryl group site thereof is the same as the foregoing aryl group having a carbon number of from 6 to 40, which is represented by $R^1$ to $R^{12}$.

Examples of the substituent include halogen atoms such as a fluorine atom, a chlorine atom, a bromine atom, an iodine atom, etc.; a hydroxyl group; alkoxy groups having preferably a carbon number of from 1 to 10 (more preferably a carbon number of from 1 to 5), such as a methoxy group, an ethoxy group, various propoxy groups, various butoxy groups, etc.; aryl groups having preferably a ring-forming carbon number of from 6 to 14, such as a phenyl group, a tolyl group, a naphthyl group, etc.; a cyano group; and so forth.

Of the subject aryloxy groups, from the viewpoints of easiness of availability of a raw material and the like, aryloxy groups having a ring-forming carbon number of from 6 to 20 are preferable; aryloxy groups having a ring-forming carbon number of from 6 to 14 are more preferable; and a phenoxy group, a naphthoxy group and a phenanthryloxy group are still more preferable.

The disubstituted amino group substituted with a group having a carbon number of from 1 to 40, which is represented by $R^1$ to $R^{12}$, is preferably a group represented by the general formula (II).

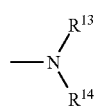

(II)

In the general formula (II), each of $R^{13}$ and $R^{14}$ independently represents a substituted or unsubstituted alkyl group having a carbon number of from 1 to 40 or a substituted or unsubstituted aryl group having a carbon number of from 6 to 40.

The substituted or unsubstituted alkyl group having a carbon number of from 1 to 40, which is represented by $R^{13}$ and $R^{14}$, may be straight chain, branched chain or cyclic. Examples of the substituent include a hydroxyl group; alkyl groups having preferably a carbon number of from 1 to 10 (more preferably a carbon number of from 1 to 5), such as a methyl group, a trifluoromethyl group, an ethyl group, various propyl groups, various butyl groups, etc.; alkoxy groups having preferably a carbon number of from 1 to 10 (more preferably a carbon number of from 1 to 5), such as a methoxy group, an ethoxy group, various propoxy groups, various butoxy groups, etc.; and so forth.

In the substituted or unsubstituted aryl group having a carbon number of from 6 to 40, which is represented by $R^{13}$ and $R^{14}$, examples of the substituent include halogen atoms such as a fluorine atom, a chlorine atom, a bromine atom, an iodine atom, etc.; a hydroxyl group; alkyl groups having preferably a carbon number of from 1 to 10 (more preferably a carbon number of from 1 to 5), such as a methyl group, a trifluoromethyl group, an ethyl group, various propyl groups, various butyl groups, etc.; alkenyl groups such as a vinyl group, a 2,2-diphenylvinyl group, a 1,2,2-triphenylvinyl group, etc.; alkoxy groups having preferably a carbon number of from 1 to 10 (more preferably a carbon number of 1 to 5), such as a methoxy group, an ethoxy group, various propoxy groups, various butoxy group, etc.; aryl groups having preferably a ring-forming carbon number of from 6 to 14, such as a phenyl group, a tolyl group, a naphthyl group, etc.; a cyano group; and so forth.

Examples of the disubstituted amino group substituted with a group having a carbon number of from 1 to 40 include a dialkylamino group, a diarylamino group, an alkylarylamino group and so forth. In the dialkylamino group, the alkyl groups bonded to the nitrogen atom may be the same as or different from each other, and specific examples thereof include a dimethylamino group, a methylethylamino group, a diethylamino group and so forth. Also, the alkyl groups may be bonded to each other to form a ring (a part of the ring may be substituted with a nitrogen atom or an oxygen atom), and specific examples thereof include nitrogen-containing heterocyclic groups having a ring-forming atom number of from 5 to 20 (preferably from 5 to 10), such as a pyrrolidinyl group, a piperidino group, a piperazinyl group, a morpholino group, etc. Specific examples of the alkylamino group having a substituent include a bis(2-hydroxyethyl)amino group, a bis (2-methoxyethyl)amino group, a pipecolino group and so forth. Of these, from the viewpoints of easiness of availability of a raw material and the like, a dimethylamino group, a diethylamino group and a piperidino group are preferable. In this connection, in the dialkylamino group, a carbon number of the alkyl group site is preferably from 1 to 20, more preferably from 1 to 10, and still more preferably from 1 to 5.

In the diarylamino group, the aryl groups bonded to the nitrogen atom may be the same as or different from each other, and specific examples thereof include a diphenylamino group, a phenyl-1-naphthylamino group, a phenyl-2-naphthylamino group and so forth. Examples of the diarylamino group having a substituent include a di-p-tolylamino group, a di-m-tolylamino group, a phenyl-m-tolylamino group, a phenyl (sec-butylphenyl)amino group, a bis(4-methoxyphenyl) amino group and so forth. Of these, from the viewpoints of easiness of availability of a raw material and the like, a diphenylamino group, a ditolylamino group and a bis(4-methoxyphenyl)amino group are preferable.

Examples of the alkylarylamino group include a methylphenylamino group, a phenyl-t-butylamino group and so forth.

As to the indenopyrene compound of the present invention, in the foregoing general formula (I), it is preferable that each of $R^1$ to $R^{12}$ other than a disubstituted amino group substituted with a group having a carbon number of from 1 to 40 is independently a hydrogen atom, a substituted or unsubstituted alkyl group having a carbon number of from 1 to 40 or a substituted or unsubstituted aryl group having a carbon number of from 6 to 40.

Also, as to the indenopyrene compound of the present invention, in the foregoing general formula (I), it is preferable that at least one member selected among $R^2$, $R^3$ and $R^9$ is a disubstituted amino group substituted with a group having a carbon number of from 1 to 40; and it is more preferable that the subject disubstituted amino group substituted with a group having a carbon number of from 1 to 40 is the disubstituted amino group represented by the general formula (II) and is a disubstituted amino group in which each of $R^{13}$ and $R^{14}$ is independently a substituted or unsubstituted aryl group having a carbon number of from 6 to 40.

Also, in these cases, it is especially preferable that $R^1$ to $R^{12}$ other than a disubstituted amino group substituted with a group having a carbon number of from 1 to 40 are a hydrogen atom.

Specific examples of the indenopyrene compound represented by the foregoing general formula (I) are shown below, but it should not be construed that the present invention is limited thereto.

-continued
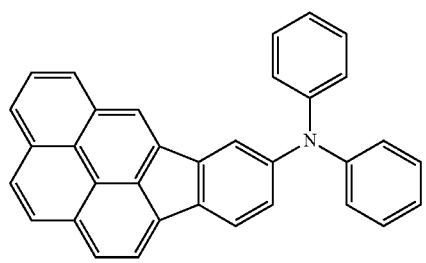
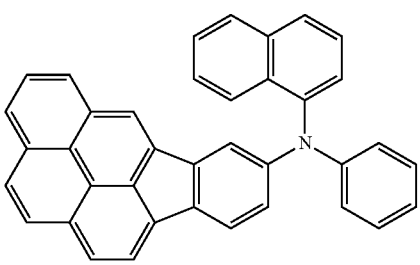
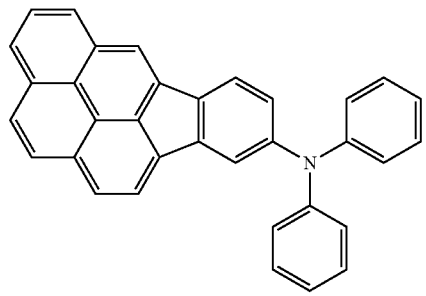
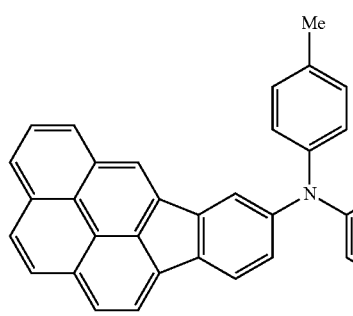
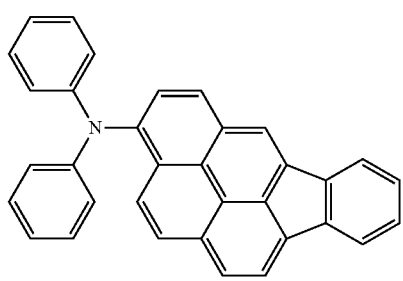
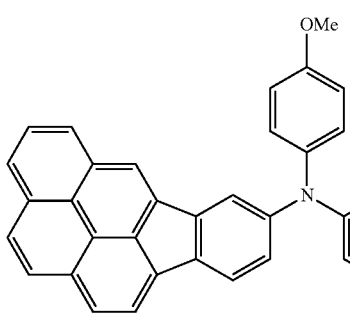
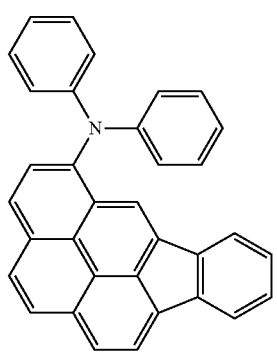
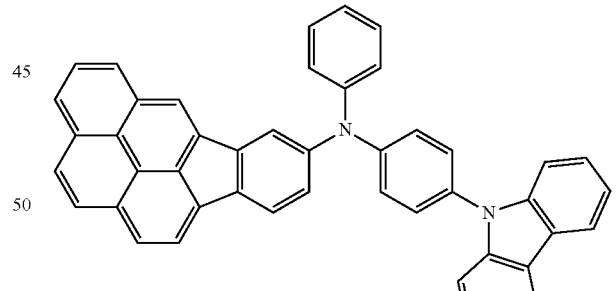
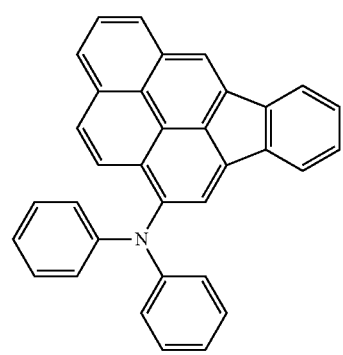
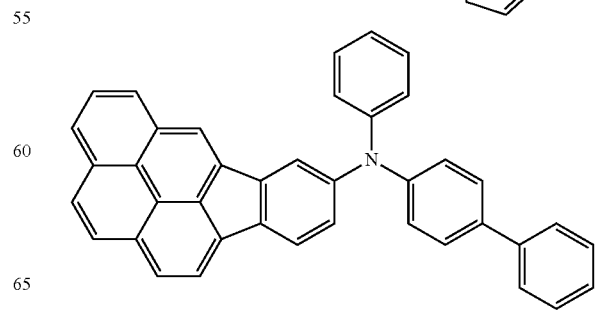

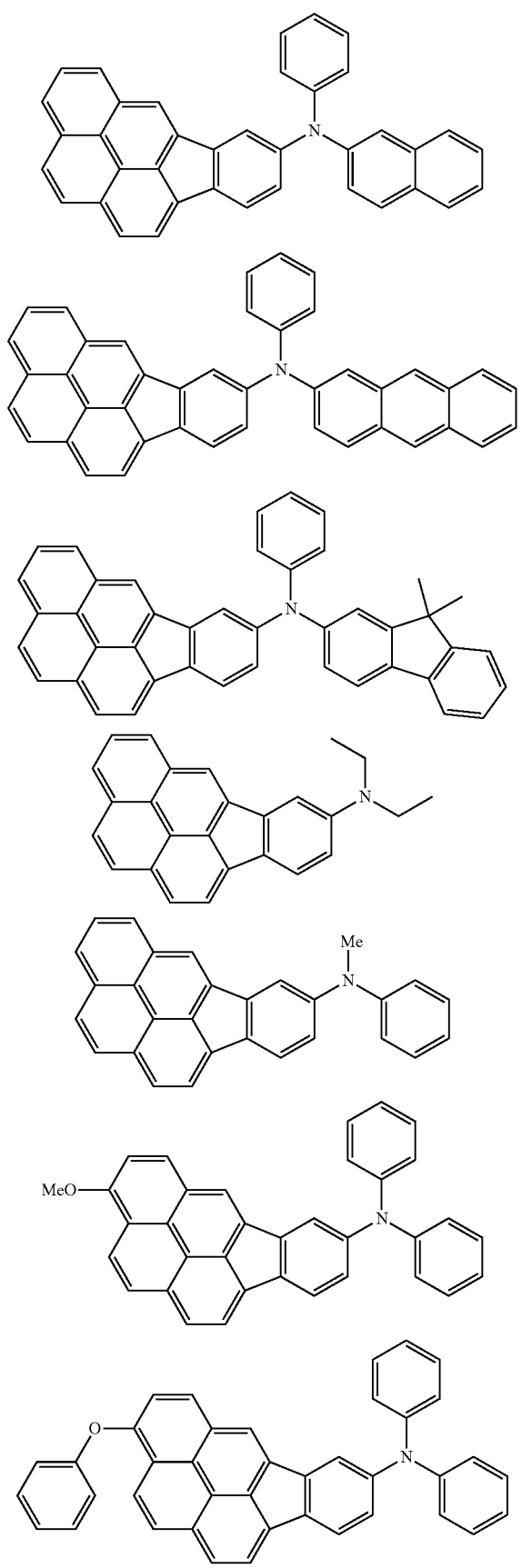
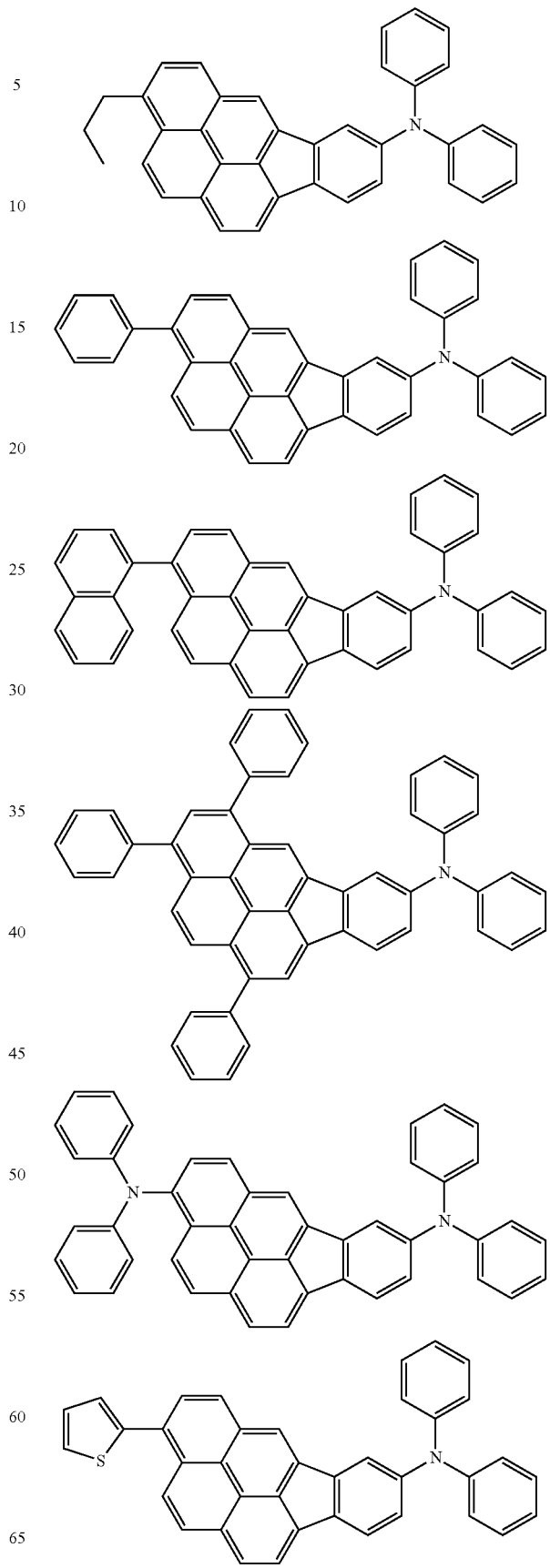

-continued

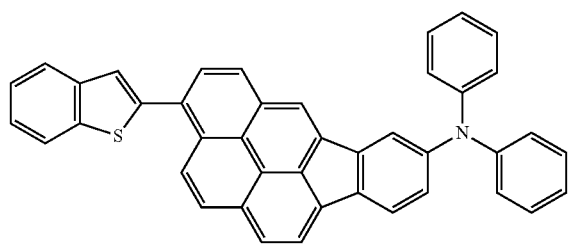

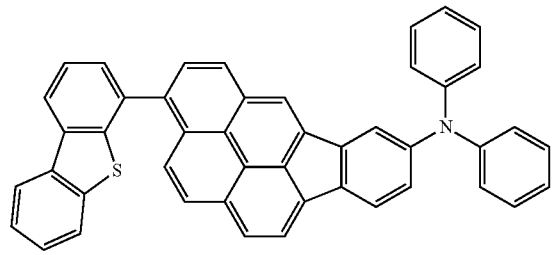

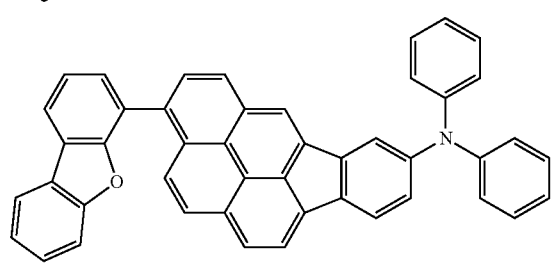

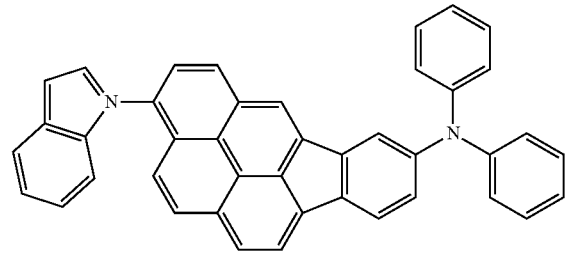

Of these, the following indenopyrene compounds are preferable.

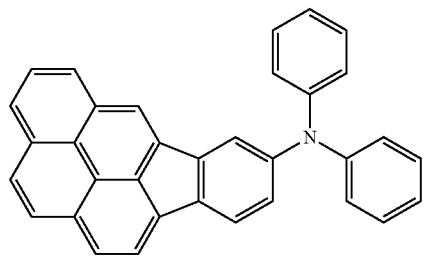

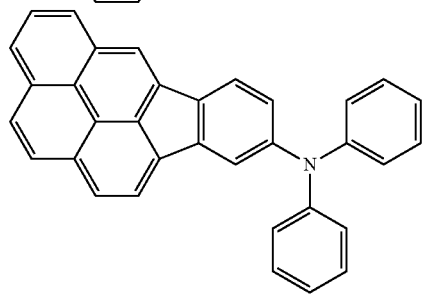

-continued

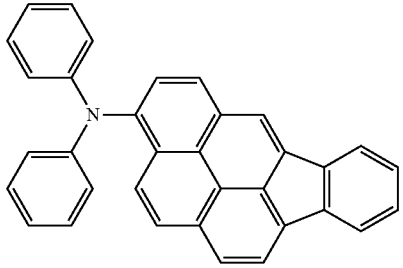

Production Method of Indenopyrene Compound

A production method of the indenopyrene compound of the present invention is not particularly limited, and for example, the subject compound can be produced by a method of performing ring closure using a metal catalyst such as palladium, etc. So far as this production method is concerned, it is preferable from the standpoints that the raw material is easily available; the reaction condition is mild; the desired material is given in a high yield; and the like.

(Ring Closure Reaction)

As the ring closure reaction, a reaction shown in the following Scheme I is exemplified.

Scheme I

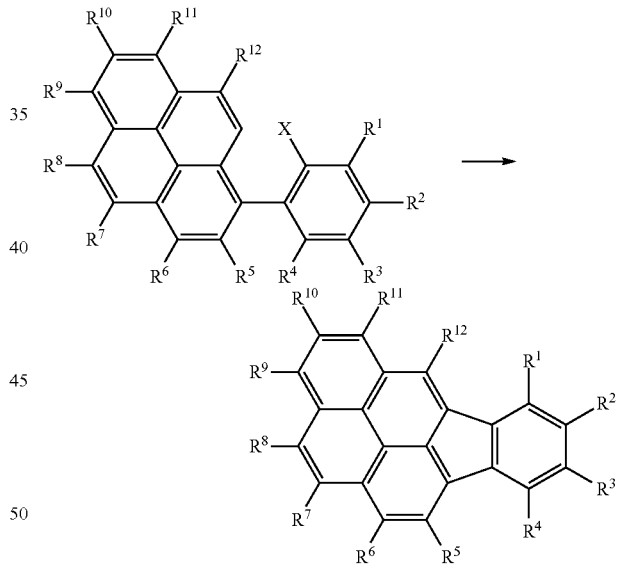

Here, X represents a halogen atom such as chlorine, bromine, iodine, etc. or a split-off group such as a trifluoromethanesulfonyloxy group, a nonafluorobutanesulfonyloxy group, a methanesulfonyloxy group, a p-toluenesulfonyloxy group, etc. Of these, in view of the fact that not only the raw material is easily available, but the yield is excellent, a halogen atom is preferable, and chlorine or bromine is especially preferable.

Examples of the metal catalyst in the ring closure reaction include divalent palladiums such as palladium chloride, palladium acetate, dichlorobis(triphenylphosphine)palladium, etc.; zero-valent palladiums such as tetrakis(triphenylphosphine)palladium, tris(dibenzylideneacetone)dipalladium, etc.; divalent nickels such as nickel chloride, dichlorobis (triphenylphosphine)nickel, dichloro(1,3-bisdiphenylphosphinopropane)nickel, etc.; and zero-valent nickels such as tetrakis(triphenylphosphine)nickel, tetracarbonylnickel, bis(cyclooctadiene)nickel, etc.

Also, a ligand can be added to such a metal catalyst. Examples of the ligand which can be used on that occasion include pyridines such as 2,2'-bipyridine, 1,10-phenanthroline, etc.; monodentate phosphines such as triphenylphosphine, tri(o-tolyl)phosphine, tri(2-furyl)phosphine, tricyclohexylphosphine, tri(t-butyl)phosphine, 2-di-t-butylphosphinobiphenyl (JohnPhos), 2-di-t-butylphosphino-2'-dimethylaminobiphenyl (DavePhos), 2-dicyclohexylphosphino-2',4',6'-triisopropyl-1,1'-biphenyl (XPhos), 2-dicyclohexylphosphino-2',6'-dimethoxybiphenyl (SPhos), etc.; bidentate phosphines such as 1,2-bis(diphenylphosphino)ethane (DPPE),1,3-bis(diphenylphosphino)propane (DPPP), 2,2'-bis(diphenylphosphino)-1,1'-binaphthyl (BINAP), 1,1'-bis(diphenylphosphino)ferrocene (DPPF), 4,5-bis(diphenylphosphino)-9,9-dimethylxanthene (XantPhos), etc.; and so forth. Of these, phosphines are preferable for the reasons that a high yield is given; and that the reaction condition is mild.

In the ring closure reaction, in order to trap hydrogen chloride and the like generated on the occasion of the reaction, it is preferable to add a base to the reaction system. Examples of the base which can be used on that occasion include inorganic bases such as potassium carbonate, cesium carbonate, potassium hydroxide, barium hydroxide, etc.; and organic bases such as 1,8-diazabicyclo[5.4.0]-7-undecene (DBU), 1,5-diaza[4.3.0]bicyclo-5-nonene (DBN), 2,4,6-trimethylpyridine, etc. Of these, organic bases are preferable for the reason that a high yield is given.

A solvent in the ring closure reaction is not particularly limited so far as it is inert against the reaction, and examples thereof include aromatic solvents such as toluene, xylene, ethylbenzene, tetralin, etc.; ethers such as tetrahydrofuran, 1,4-dioxane, etc.; amides such as N,N-dimethylformamide (DMF), N-methylpyrrolidone (NMP), etc.; and sulfoxides such as dimethyl sulfoxide (DMSO), etc. Of these, in view of the fact that a high yield is given, amides such as N,N-dimethylformamide, etc. are preferable.

A reaction temperature of the present reaction is usually from room temperature to 200° C., and preferably from 100° C. to 200° C. A reaction time is usually from 1 hour to 72 hours, and preferably from 6 hours to 24 hours.

As a synthesis method of an aryl-substituted pyrene which is a raw material of the foregoing ring closure reaction, though various methods are included, for example, the following cross coupling reactions using an organometallic reagent can be exemplified.

Scheme II

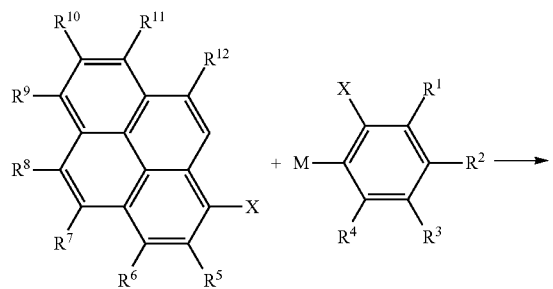

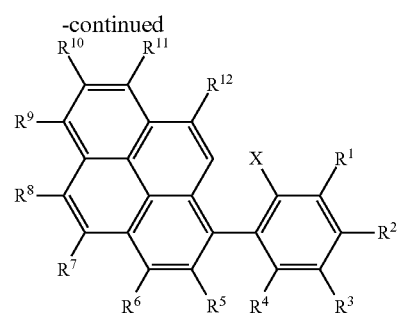

Scheme III

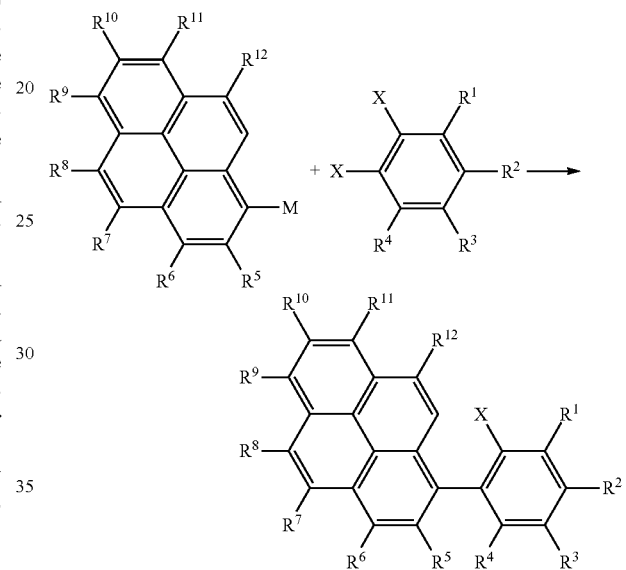

Here, X represents a halogen atom such as chlorine, bromine, iodine, etc. or a split-off group such as a trifluoromethanesulfonyloxy group, a nonafluorobutanesulfonyloxy group, a methanesulfonyloxy group, a p-toluenesulfonyloxy group, etc.; and M represents a typical metal group represented by a Grignard reagent such as MgCl, MgBr, MgI, etc., an organic zinc reagent such as ZnCl, ZnBr, etc., a boronic acid and an ester reagent thereof such as a pinacolate boryl group, a catechol boryl group, etc., an organic tin reagent such as $Sn(Bu)_4$, etc. and an organic silicon reagent such as $Si(OH)_3$, etc. The typical metal group may be bonded to the aryl group (Scheme II) or may be bonded to the pyrene (Scheme III). In these reactions, reactions such as the Kumada-Tamao coupling (Grignard reagent), the Negishi coupling (organic zinc reagent), the Suzuki-Miyaura coupling (boron reagent), the Kosugi-Migita-Stille coupling (organic tin reagent), the Hiyama coupling (organic silicon reagent), etc. can be adopted.

<Organic Thin Film Solar Cell>

The indenopyrene compound of the present invention can be used as the organic thin film solar cell material. In that case, the member (layer) of the organic thin film solar cell may be made of the indenopyrene compound of the present invention singly or may be made of a mixture of the indenopyrene compound of the present invention and other component. The organic thin film solar cell using the indenopyrene compound of the present invention displays a photoelectric conversion characteristic with high efficiency.

Though a cell structure of the organic thin film solar cell of the present invention is not particularly limited so far as it is a structure containing the organic thin film solar cell material of the present invention between a pair of electrodes, the organic thin film solar cell material of the present invention is especially suitably used as a component of the p-layer.

Specifically, as the cell structure of the organic thin film solar cell of the present invention, there are exemplified structures having the following configuration on a stable insulating substrate.

(1) Lower electrode/organic compound layer/upper electrode (2) Lower electrode/p-layer/n-layer/upper electrode (3) Lower electrode/p-layer/i-layer (mixed layer of a material of the p-layer and a material of the n-layer)/n-layer/upper electrode (4) Lower electrode/mixed layer of a material of the p-layer and a material of the n-layer/upper electrode (5) Lower electrode/[repeated layer of p-layer/(i-layer)/n-layer]/upper electrode Also, there are exemplified structures in which the p-layer and the n-layer of each of the foregoing configurations (2) and (3) are substituted with each other.

Also, as the need arises, a buffer layer may be provided between the electrodes. For example, as specific examples thereof, in the case where the buffer layer is provided in the foregoing configuration (1), structures having the following configuration are exemplified.

(6) Lower electrode/buffer layer/organic compound layer/upper electrode (7) Lower electrode/organic compound layer/buffer layer/upper electrode (8) Lower electrode/buffer layer/organic compound layer/buffer layer/upper electrode For example, the organic thin film solar cell material of the present invention can be used as a material of the organic compound layer, p-layer, n-layer, i-layer or buffer layer in the organic thin film solar cell having the foregoing structure.

In the organic thin film solar cell of the present invention, it would be good to incorporate the organic thin film solar cell material of the present invention into any one of the members (layers) constructing the organic thin film solar cell. Also, the member (layer) containing the material of the present invention may contain other component. As a material of the layer that does not contain the organic thin film solar cell material of the present invention or a material of the layer to be mixed with the organic thin film solar cell material of the present invention, known materials which are used for organic thin film solar cells can be used.

Next, each of the members (layers) which can be used in the foregoing configurations is described.

(Lower Electrode and Upper Electrode)

The material of each of the lower electrode and the upper electrode is not particularly limited, and known conductive materials can be used.

For example, metals such as a tin-doped indium oxide (ITO), gold (Au), osmium (Os), palladium (Pd), etc. can be used for the electrode to be connected to the p-layer. Also, single-component metals such as silver (Ag), aluminum (Al), indium (In), calcium (Ca), platinum (Pt), lithium (Li), etc.; two-component metals such as magnesium (Mg)—Ag, Mg—In, Al—Li, etc.; and further, the metals exemplified above for the electrode to be connected to the p-layer can be used for the electrode to be connected to the n-layer.

In this connection, a preferred configuration of a pair of electrode configurations is a configuration in which one of the electrode parts contains a metal having a large work function, and the other contains a metal having a small work function. Examples of the electrode material having a large work function include ITO, Os, Pd and so forth, and examples of the electrode material having a small work function include Al, In, an Mg—Ag alloy, Ca, Li, Mg and so forth.

In order to obtain a photoelectric conversion characteristic with high efficiency, it is desirable to make at least one surface of the solar cell sufficiently transparent in a sunlight spectrum. For that end, it would be good to form the electrode by using a known conductive material, thereby ensuring prescribed translucency by a method such as vapor deposition, sputtering, etc. A light transmittance of the electrode of the light-receiving surface is preferably 10% or more, more preferably 60% or more, and still more preferably 90% or more.

Though a film thickness can be properly chosen depending upon the material, it is preferably from 1 nm. to 10 μm, and more preferably from 5 nm to 1 μm.

(Organic Compound Layer)

The foregoing organic compound layer refers to the case where the layer between the electrodes is a single layer. Examples of the configuration of the case of using the organic thin film solar cell material of the present invention include "lower electrode/single layer made of the organic thin film solar cell material of the present invention/upper electrode" and "lower electrode/mixed layer made of the organic thin film solar cell material of the present invention and the n-layer material or p-layer material/upper electrode".

(p-Layer, n-Layer and i-Layer)

When the organic thin film solar cell material of the present invention is used for the p-layer, though the n-layer is not particularly limited, a compound having a function as an electron acceptor is preferable. So far as a low-molecular weight organic compound is concerned, examples thereof include fullerenes such as $C_{60}$, $C_{70}$, etc., carbon nanotubes, perylene derivatives, polycyclic quinones, quinacridones and so forth; and so far as a polymer compound is concerned, examples thereof include CN-poly(phenylene-vinylene), MEH-CN-PPV, —CN group-containing or $CF_3$ group-containing polymers, poly(fluorene) derivatives and so forth. A material with high electron mobility is preferable, and a material with small electron affinity is more preferable. By combining such a material with small electron affinity for the n-layer, it is possible to realize a sufficient open circuit voltage. Also, so far as an inorganic compound is concerned, inorganic semiconductor compounds with an n-type characteristic can be exemplified. Specific examples thereof include doping semiconductors and compound semiconductors such as n-Si, GaAs, CdS, PbS, CdSe, InP, $Nb_2O_5$, $WO_3$, $Fe_2O_3$, etc.; titanium oxides such as titanium dioxide ($TiO_2$), titanium monoxide (TiO), titanium trioxide ($Ti_2O_2$), etc.; and conductive oxides such as zinc oxide (ZnO), tin oxide ($SnO_2$), etc. These compounds may be used singly or in combinations of two or more kinds thereof. Titanium oxides are preferably used, and titanium dioxide is especially preferably used.

When the organic thin film solar cell material of the present invention is used for the n-layer, though the p-layer is not particularly limited, a compound having a function as a hole acceptor is preferable. So far as a low-molecular weight organic compound is concerned, examples thereof include amine compounds represented by N,N'-bis(3-tolyl)-N,N'-diphenylbenzidine (mTPD), N,N'-dinaphthyl-N,N'-diphenylbenzidine (NPD), 4,4',4''-tris(phenyl-3-tolylamino)triphenylamine (MTDATA), etc.; phthalocyanines such as phthalocyanine (Pc), copper phthalocyanine (CuPc), zinc phthalocyanine (ZnPc), titanyl phthalocyanine (TiOPc), etc.; and porphyrins represented by octaethyl porphyrin (OEP), platinum octaethyl porphyrin (PtOEP), zinc tetraphenyl porphyrin (ZnTPP), etc. So far as a polymer compound is concerned, examples thereof include main chain type conjugated polymers such as polyhexylthiophene (P3HT), methoxyethylhexyloxyphenylene vinylene (MEHPPV), etc.; side chain type polymers such as polyvinylcarbazole, etc.; and so forth.

When the organic thin film solar cell material of the present invention is used for the i-layer, though it may be mixed with the foregoing p-layer compound or n-layer compound to form the i-layer, the material of the present invention can be used singly for the i-layer. In that case, all of the foregoing exemplified compounds can be used for the p-layer or n-layer.

In the case of mixing the material of the present invention to form the i-layer, a mixing ratio of the material of the n-layer to the material of the p-layer is preferably from 1/5 to 5/1, more preferably from 1/2 to 2/1, and still more preferably from 0.9/1.1 to 1.1/0.9 in terms of a volume ratio.

In the organic thin film solar cell of the present invention, in the case where the p-layer is provided, its film thickness is preferably from 5 nm to 5 μm, and more preferably from 10 nm to 1 μm; in the case where the n-layer is provided, its film thickness is preferably from 5 nm to 5 μm, and more preferably from 10 nm to 1 μm; and in the case where the i-layer is provided, its film thickness is preferably from 1 nm to 2 μm, and more preferably from 5 nm to 1 μm.

(Buffer Layer)

In general, since a total film thickness of the organic thin film solar cell is thin, in many cases, the upper electrode and the lower electrode cause a short circuit, and a yield of the cell fabrication is lowered. In such case, it is preferable to prevent this from occurring by laminating a buffer layer. Also, it is preferable to provide the buffer layer for the purpose of efficiently taking out a generated current externally.

As a preferred compound for the buffer layer, a compound with sufficiently high carrier mobility such that even when the film thickness is thick, the short-circuit current is not lowered is preferable. So far as a low-molecular weight compound is concerned, examples thereof include aromatic cyclic acid anhydrides represented by the following NTCDA; and so forth. So far as a polymer compound is concerned, examples thereof include known conductive polymers such as poly (3,4-ethylenedioxy)thiophene/the following polystyrene sulfonate (PEDOT:PSS); polyaniline/camphor sulfonic acid (PANI:CSA); and so forth.

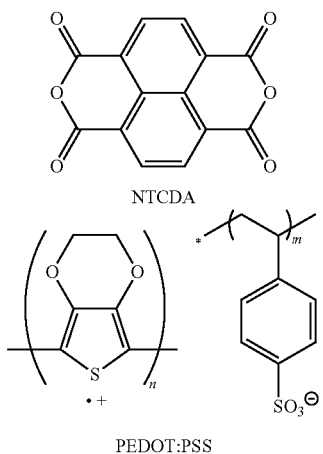

Also, it is possible to bear a role to prevent deactivation to be caused due to the fact that an exciton is diffused into the electrode on the buffer layer. What the buffer layer is inserted as an exciton blocking layer in this way is effective for realizing high efficiency. In the case of bearing a role as an exciton blocking layer on the buffer layer, examples of a preferred material include hole blocking layer materials or electron blocking layer materials which are known for organic electroluminescence (organic EL) applications, and so forth. The material which is preferably utilized for the hole blocking layer is a compound with sufficiently large ionization potential; and the material which is preferably utilized for the electron blocking layer is a compound with sufficiently small electron affinity. Specific examples of the hole blocking layer material on the cathode side include the following Bathocuproin (BCP), the following Bathophenanthroline (BPhen) and so forth.

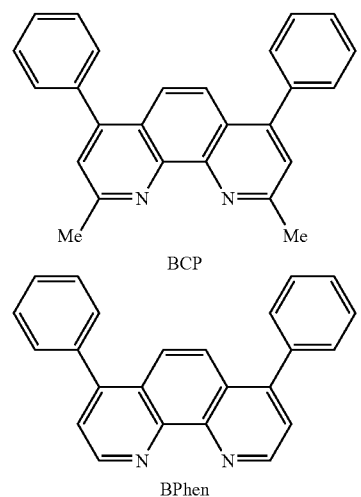

Furthermore, the inorganic compounds exemplified as the material of the n-layer may be used for the butter layer. Also, CdTe, p-type silicon (p-Si), SiC, GaAs and $WO_3$, each of which is a known inorganic compound with a p-type characteristic, and so forth may be used.

A film thickness of the buffer layer is preferably from 1 nm to 3 μm, and more preferably from 5 nm to 1 μm.

In this connection, in the case where the cell structure of the organic thin film solar cell is "lower electrode/single layer made of the organic thin film solar cell material of the present invention/upper electrode", a film thickness of the single layer is preferably from 1 nm to 10 μm, and more preferably from 5 nm to 1 μm.

(Substrate)

The substrate may be a substrate which is usually used for organic thin film solar cells. It is preferable to use a glass substrate or a transparent resin film having mechanical and thermal strengths and having transparency.

Examples of the transparent resin film include polyethylene, an ethyl/vinyl acetate copolymer, an ethylene/vinyl alcohol copolymer, polypropylene, polystyrene, polymethyl methacrylate, polyvinyl chloride, polyvinyl alcohol, polyvinyl butyral, nylon, polyetheretherketone, polysulfone, polyether sulfone, a tetrafluoroethylene/perfluoroalkyl vinyl ether copolymer, polyvinyl fluoride, a tetrafluoroethylene/ethylene copolymer, a tetrafluoroethylene/hexafluoropropylene copolymer, polychlorotrifluoroethylene, polyvinylidene fluoride, polyesters, polycarbonates, polyurethane, polyimides, polyether imides, polyimides, polypropylene and so forth.

(Forming Method of Each Layer of Organic Thin Film Solar Cell)

A forming method of each layer of the organic thin film solar cell of the present invention is not particularly limited, and dry film deposition methods such as vacuum vapor deposition, sputtering, plasma, ion plating, etc., or wet film deposition methods such as spin coating, dip coating, casting, roll coating, flow coating, inkjetting, etc. can be adopted. It is preferable to regulate each layer to the foregoing film thickness of each layer according to this method. In general, since it is known that an exciton diffusion length of an organic thin film is short, when the film thickness is too thick, deactivation is caused before the exciton reaches a hetero-interface, so that the photoelectric conversion efficiency becomes low. When the film thickness is too thin, since pinholes or the like are generated, a sufficient diode characteristic is not obtained, so that the conversion efficiency is lowered.

In the case of adopting the foregoing dry film deposition method, it is preferable to heat and vaporize the material by adopting a resistance heating method. Also, in the case of forming a mixed layer, for example, a film deposition method by simultaneous vapor deposition from plural vaporization sources is preferable. At the time of film deposition, it is preferable to control a substrate temperature on a fixed level.

In the case of adopting the foregoing wet film deposition method, after the material is dissolved or dispersed in an appropriate solvent to prepare a light-emitting organic solution, the thin film is formed. As such a solvent, an arbitrary solvent can be used. Examples thereof include halogen based hydrocarbon based solvents such as dichloromethane, dichloroethane, chloroform, carbon tetrachloride, tetrachloroethane, trichloroethane, chlorobenzene, dichlorobenzene, chlorotoluene, etc.; ether based solvents such as dibutyl ether, tetrahydrofuran, dioxane, anisole, etc.; alcohol based solvents such as methanol, ethanol, propanol, butanol, pentanol, hexanol, cyclohexanol, methyl cellosolve, ethyl cellosolve, ethylene glycol, etc.; hydrocarbon based solvents such as benzene, toluene, xylene, ethylbenzene, hexane, octane, decane, tetralin, etc.; ester based solvents such as ethyl acetate, butyl acetate, amyl acetate, etc.; and so forth. Of these, hydrocarbon based solvents or ether based solvents are preferable. Also, such a solvent may be used singly or in admixture of plural kinds thereof. In this connection, it should not be construed that the solvent is limited thereto.

In the present invention, for the purposes of enhancing film deposition properties, preventing the formation of pinholes of the film and so on, any of the organic thin film layers of the organic thin film solar cell may contain an appropriate resin or additive. Examples of the resin which can be used include insulating resins such as polystyrene, polycarbonates, polyarylates, polyesters, polyamides, polyurethane, polysulfone, polymethyl methacrylate, polymethyl acrylate, cellulose, etc., and copolymers thereof; photoconductive resins such as poly-N-vinylcarbazole, polysilanes, etc.; conductive resins such as polythiophene, polypyrrole, etc.; and so forth.

Also, examples of the additive include an antioxidant, an ultraviolet light absorber, a plasticizer and so forth.

The organic thin film solar cell using the organic thin film solar cell material obtained in the present invention is effectively utilized for apparatuses such as solar cell modules, solar panels, clocks or watches, personal digital assistants, personal computers, etc.

EXAMPLES

Next, the present invention is described in more detail with reference to the following Examples, but it should not be construed that the present invention is limited to these Examples.

In this connection, in each of the Examples, an I-V characteristic was measured under an AM1.5 condition (light intensity: 100 mW/cm$^2$) using a solar simulator (apparatus name: SS-50XIL, manufactured by EKO Instruments Co., Ltd.), and an open circuit voltage (Voc), a short-circuit current density (Jsc), a fill factor (FF) and a conversion efficiency ($\eta$) were determined. A compound which is large in all of Voc, Jsc and FF at the same Pin (light intensity) displays an excellent conversion efficiency. In this connection, the photoelectric conversion efficiency was derived according to the following expression.

$$\eta\ (\%) = \frac{Voc \times Jsc \times FF}{Pin} \times 100$$

Production Example 1

The following Indenopyrene Compound A was produced through the following synthesis route.

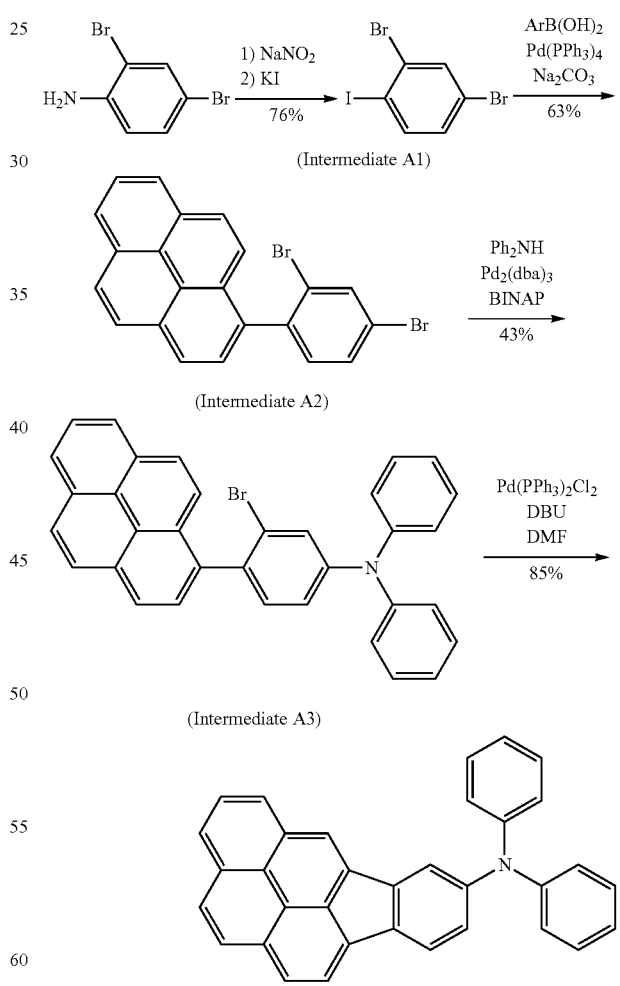

Synthesis of Intermediate A1

2,4-Dibromoaniline (10 g, 40 mmoles) was suspended in hydrochloric acid water (40 mL of concentrated hydrochloric acid and 30 mL of water), and the suspension was cooled on an ice/salt bath at −8° C. A sodium nitrite aqueous solution (3.0 g, 43 mmoles, 1.1 eq./15 mL) was gradually added dropwise thereto over 10 minutes, and the mixture was stirred at from −10° C. to 0° C. for 30 minutes, thereby preparing a diazonium salt. The reaction solution was gradually added dropwise to a potassium iodide aqueous solution (60 g, 0.36 moles, 9 eq./180 mL) at room temperature over 20 minutes. The reaction mixture was stirred at room temperature for 3 hours, to which was then added dichloromethane (200 mL), and subsequently, sodium hydrogensulfite (2 g) was added, thereby deactivating generated iodine. An organic layer was aliquoted, washed with a sodium hydrogensulfite aqueous solution (100 mL) and saturated salt water (30 mL) and then dried over anhydrous magnesium sulfate, and the solvent was then distilled off to obtain a red liquid. This was purified by means of column chromatography (silica gel/hexane) to obtain a white solid (11.0 g, 76%).

$^1$H-NMR (400 MHz, CDCl$_3$, TMS): δ7.11 (1H, dd, J=8 Hz, 2 Hz), 7.69 (1H, d, J=8 Hz), 7.76 (1H, d, J=2 Hz)

Synthesis of Intermediate A2

Intermediate A1 (2.5 g, 6.9 mmoles), 1-pyreneboronic acid (1.7 g, 6.9 mmoles) and tetrakis(triphenylphosphine)palladium(0) (0.24 g, 0.21 mmoles, 3% Pd) were suspended in 1,2-dimethoxyethane (20 mL) under a nitrogen atmosphere, to which was then added a 2M sodium carbonate aqueous solution (2.2 g, 21 mmoles, 3 eq./10 mL), and the mixture was refluxed for 10 hours. Toluene (150 mL) and water (50 mL) were added to the reaction mixture, an organic layer was aliquoted, washed with saturated saltwater (50 mL) and then dried over anhydrous magnesium sulfate, and the solvent was distilled off to obtain a pale yellow solid. This was purified by means of column chromatography (silica gel/hexane and 17% dichloromethane) to obtain a white solid (1.9 g, 63%).

$^1$H-NMR (400 MHz, CDCl$_3$, TMS): δ7.32 (1H, d, J=8 Hz), 7.60 (1H, dd, J=8 Hz, 2 Hz), 7.68 (1H, d, J=9 Hz), 7.83 (1H, d, J=8 Hz), 7.96 to 8.02 (3H, m), 8.10 (2H, s), 8.16 (1H, d, J=8 Hz), 8.20 (1H, d, J=8 Hz), 8.21 (1H, d, J=8 Hz)

Synthesis of Intermediate A3

Intermediate A2 (3.3 g, 7.6 mmoles), diphenylamine (1.4 g, 8.3 mmoles, 1.1 eq.), tris(dibenzylideneacetone)dipalladium(0) (0.10 g, 0.11 mmoles, 3% Pd), 2,2'-bis(diphenylphosphino)-1,1'-binaphthyl (BINAP, 0.20 g, 0.32 mmoles, 1.5 eq. to Pd) and sodium t-butoxide (1.0 g, 10 mmoles, 1.4 eq.) were suspended in anhydrous toluene (20 mL) under a nitrogen atmosphere, and the suspension was refluxed for 10 hours. The reaction mixture was filtered off by passing through a silica gel pad and then washed with toluene (200 mL). A brown oil obtained by distilling off the solvent from the filtrate was purified by means of column chromatography (silica gel/hexane and 17% dichloromethane and subsequently, hexane and 33% dichloromethane) to obtain a pale orange solid (1.7 g, 43%).

$^1$H-NMR (400 MHz, CDCl$_3$, TMS): δ7.09 to 7.15 (3H, m), 7.23 to 7.25 (4H, m), 7.29 (1H, dd, J=9 Hz, 2 Hz), 7.35 (4H, t, J=8 Hz), 7.50 (1H, s), 7.87 (1H, d, J=9 Hz), 7.93 (1H, dd, J=8 Hz, 2 Hz), 8.01 (1H, dt, J=8 Hz, 1 Hz), 8.05 (1H, d, J=9 Hz), 8.10 (2H, s), 8.17 to 8.23 (3H, m)

Synthesis of Indenopyrene Compound A
(Hereinafter Sometimes Abbreviated as "Compound A")

Intermediate A3 (1.7 g, 3.2 mmoles), dichlorobis(triphenylphosphine)palladium(II) (0.23 g, 0.33 mmoles, 10% Pd) and 1,8-diazabicyclo[5.4.0]-7-undecene (0.7 g, 4.6 mmoles, 1.4 eq.) were dissolved in anhydrous DMF (15 mL) under a nitrogen atmosphere, and the solution was stirred at 140° C. for 11 hours. The reaction mixture was diluted with toluene (150 mL), washed with water (100 mL) and saturated salt water (50 mL) and then dried over anhydrous magnesium sulfate, and the solvent was distilled off. The thus obtained red solid was purified by means of column chromatography (silica gel/hexane and 10% dichloromethane and subsequently, hexane and 17% dichloromethane) to obtain an orange solid (1.2 g, 85%). This was recrystallized from ethanol (30 mL) and toluene (100 mL) to obtain an orange needle crystal (1.0 g).

$^1$H-NMR (400 MHz, CDCl$_3$, TMS): δ7.06 (2H, t, J=7 Hz), 7.18 to 7.25 (5H, m), 7.31 (4H, t, J=8 Hz), 7.87 to 7.89 (2H, m), 7.99 (1H, d, J=8 Hz), 8.03 (1H, d, J=8 Hz), 8.10 (1H, d, J=9 Hz), 8.20 (1H, d, J=8 Hz), 8.22 (1H, d, J=7 Hz), 8.28 (1H, d, J=8 Hz), 8.31 (1H, d, J=8 Hz), 8.42 (1H, s)

FDMS: Calculated for C$_{34}$H$_{21}$N=443, found value m/z=443 (M$^+$, 100)

HPLC: 99.5% (UV254, in percent by area)

A solid (1.0 g) obtained by the foregoing method was subjected to sublimation and purification at 280° C. and 3.2× 10$^{-4}$ Pa, thereby obtaining a red amorphous solid (0.9 g).

HPLC: 99.6% (UV254, in percent by area)

Melting point: 207° C. (DSC)

Absorption maximum wavelength (CH$_2$Cl$_2$): 471 nm

Fluorescence maximum wavelength (CH$_2$Cl$_2$): 597 nm

Production Example 2

The following Indenopyrene Compound B was produced through the following synthesis route.

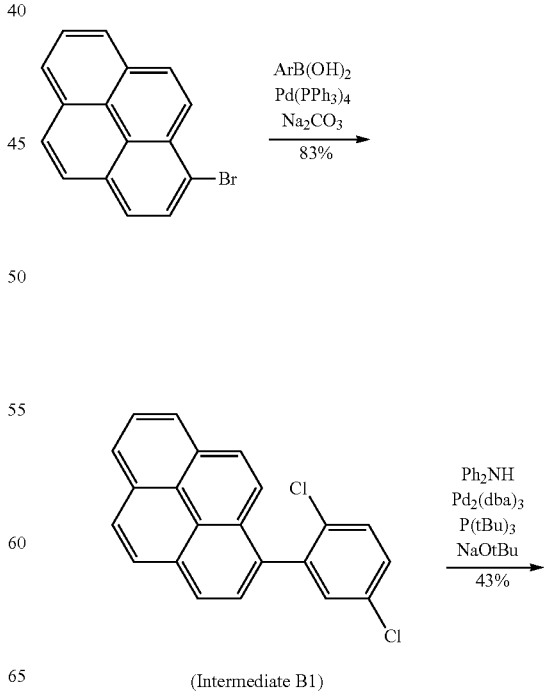

(Intermediate B1)

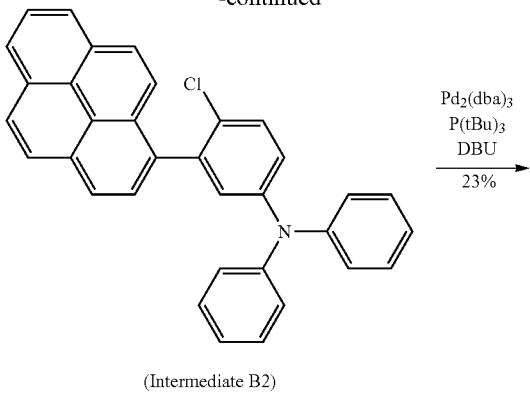

(Intermediate B2)

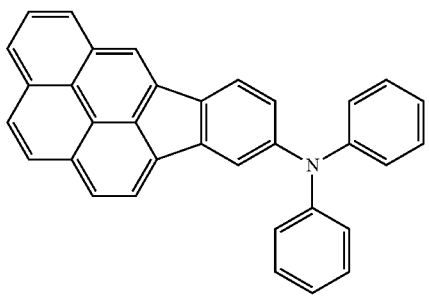

Synthesis of Intermediate B1

1-Bromopyrene (5.0 g, 18 mmoles), 2,5-dichlorophenylboronic acid (4.1 g, 21 mmoles, 1.2 eq.) and tetrakis(triphenylphosphine)palladium(0) (0.40 g, 0.35 mmoles, 2% Pd) were suspended in 1,2-dimethoxyethane (65 mL) under a nitrogen atmosphere, to which was then added a 2M sodium carbonate aqueous solution (6.7 g, 63 mmoles, 3 eq./30 mL), and the mixture was refluxed for 10 hours. Toluene (100 mL) and water (50 mL) were added to the reaction mixture, an organic layer was aliquoted, washed with saturated salt water (50 mL) and then dried over anhydrous magnesium sulfate, and the solvent was distilled off to obtain a pale yellow oil. This was purified by means of column chromatography (silica gel/hexane and 17% dichloromethane) to obtain a white solid (5.2 g, 83%).

$^1$H-NMR (400 MHz, CDCl$_3$, TMS): δ7.40 (1H, dd, J=9 Hz, 2 Hz), 7.49 (1H, d, J=2 Hz), 7.51 (1H, d, J=9 Hz), 7.71 (1H, d, J=9 Hz), 7.86 (1H, d, J=8 Hz), 8.00 (1H, t, J=8 Hz), 8.02 (1H, d, J=9 Hz), 8.08 (1H, d, J=9 Hz), 8.11 (1H, d, J=9 Hz), 8.16 (1H, d, J=8 Hz), 8.20 (1H, d, J=7 Hz), 8.21 (1H, d, J=8 Hz)

Synthesis of Intermediate B2

Intermediate B1 (5.2 g, 15 mmoles), diphenylamine (2.8 g, 17 mmoles, 1.1 eq.), tris(dibenzylideneacetone)dipalladium (0) (0.14 g, 0.15 mmoles, 2% Pd), a tri-t-butylphosphine/toluene solution (66% by weight, 0.07 mL, 0.23 mmoles, 0.8 eq. to Pd) and sodium t-butoxide (2.0 g, 21 mmoles, 1.4 eq.) were suspended in anhydrous toluene (40 mL) under a nitrogen atmosphere, and the suspension was refluxed for 10 hours. The reaction mixture was filtered off by passing through a silica gel pad and then washed with toluene (200 mL). A brown oil obtained by distilling off the solvent from the filtrate was purified by means of column chromatography (silica gel/hexane and 17% dichloromethane and subsequently, hexane and 33% dichloromethane) to obtain a yellowish orange amorphous solid (5.9 g, 82%).

$^1$H-NMR (400 MHz, CDCl$_3$, TMS): δ7.05 (2H, t, J=7 Hz), 7.18 to 7.33 (11H, m), 7.74 to 8.14 (6H, m), 8.20 to 8.26 (3H, m)

Synthesis of Indenopyrene Compound B (Hereinafter Sometimes Abbreviated as "Compound B")

Intermediate B2 (5.9 g, 12 mmoles), tris(dibenzylideneacetone)dipalladium(0) (0.28 g, 0.31 mmoles, 5% Pd), a tri-t-butylphosphine/toluene solution (66% by weight, 0.19 mL, 0.62 mmoles, 1 eq. to Pd) and 1,8-diazabicyclo[5.4.0]-7-undecene (2.6 g, 17 mmoles, 1.4 eq.) were dissolved in anhydrous DMF (30 mL) under a nitrogen atmosphere, and the solution was stirred at 140° C. for 11 hours. The reaction mixture was diluted with toluene (150 mL), washed with water (100 mL) and saturated salt water (50 mL) and then dried over anhydrous magnesium sulfate, and the solvent was distilled off. The thus obtained reddish brown solid was purified by means of column chromatography (silica gel/hexane and 10% dichloromethane and subsequently, hexane and 33% dichloromethane) to obtain an orange solid (3.5 g, 66%). This was recrystallized from ethanol (20 mL) and toluene (50 mL) to obtain an orange tabular crystal (1.2 g, 23%).

$^1$H-NMR (400 MHz, CDCl$_3$, TMS): δ7.07 (1H, d, J=7 Hz), 7.12 (1H, dd, J=8 Hz, 2 Hz), 7.23 (4H, d, J=7 Hz), 7.31 (4H, t, J=7 Hz), 7.76 (1H, d, J=2 Hz), 7.97 (1H, d, J=8 Hz), 8.01 to 8.12 (3H, m), 8.16 to 8.25 (3H, m), 8.38 (1H, d, J=7 Hz), 8.46 (1H, s)

FDMS: Calculated for C$_{34}$H$_{21}$N=443, found value m/z=443 (M$^+$, 100)

HPLC: 99.6% (UV254, in percent by area)

A solid (1.0 g) obtained by the foregoing method was subjected to sublimation and purification at 300° C. and 1.5× 10$^{-4}$ Pa, thereby obtaining an orange solid (0.87 g).

HPLC: 99.8% (UV254, in percent by area)

Melting point: 234° C. (DSC)

Absorption maximum wavelength (CH$_2$Cl$_2$): 420 nm

Fluorescence maximum wavelength (CH$_2$Cl$_2$): 569 nm

Production Example 3

The following Indenopyrene Compound C was produced through the following synthesis route.

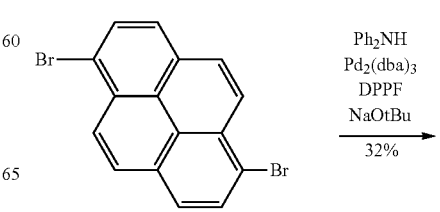

-continued

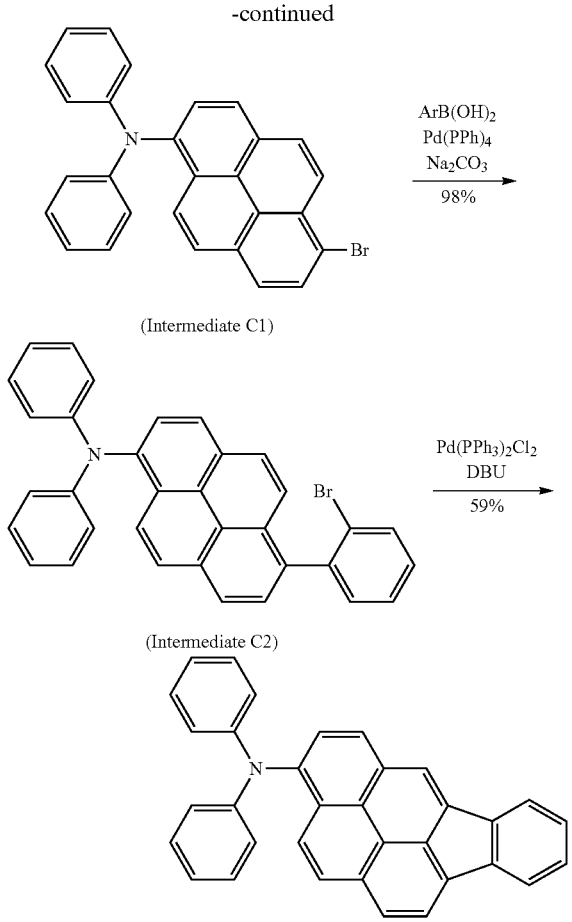

Synthesis of Intermediate C1

1,6-Dibromopyrene (5.0 g, 14 mmoles), diphenylamine (2.3 g, 14 mmoles), tris(dibenzylideneacetone)dipalladium (0) (0.19 g, 0.21 mmoles, 3% Pd), 1,1'-bis(diphenylphosphino)ferrocene (DPPE, 0.34 g, 0.61 mmoles, 1.5 eq. to Pd) and sodium t-butoxide (1.9 g, 20 mmoles, 1.4 eq.) were suspended in anhydrous toluene (40 mL) under a nitrogen atmosphere, and the suspension was refluxed for 11 hours. The reaction mixture was filtered off by passing through a silica gel pad and then washed with toluene (200 mL). A brown oil obtained by distilling off the solvent from the filtrate was purified by means of column chromatography (silica gel/hexane and 17% dichloromethane and subsequently, hexane and 33% dichloromethane) to obtain a yellow solid (2.0 g, 32%).

$^1$H-NMR (400 MHz, CDCl$_3$, TMS): δ6.96 (2H, t, J=7 Hz), 7.06 (4H, d, J=7 Hz), 7.20 (4H, t, J=7 Hz), 7.85 (1H, d, J=8 Hz), 7.86 (1H, d, J=9 Hz), 7.92 (1H, d, J=8 Hz), 8.10 to 8.21 (4H, m), 8.41 (1H, d, J=9 Hz)

Synthesis of Intermediate C2

Intermediate C1 (2.0 g, 4.5 mmoles), 2-bromophenylboronic acid (1.1 g, 5.5 mmoles, 1.2 eq.) and tetrakis(triphenylphosphine)palladium(0) (0.10 g, 87 μmoles, 2% Pd) were suspended in 1,2-dimethoxyethane (20 mL) under a nitrogen atmosphere, to which was then added a 2M sodium carbonate aqueous solution (1.7 g, 16 mmoles, 3 eq./8 mL), and the mixture was refluxed for 11 hours. The reaction mixture was diluted with water (100 mL), and a solid was filtered off and then washed with water and methanol to obtain a yellow solid (2.3 g, 98%).

$^1$H-NMR (400 MHz, CDCl$_3$, TMS): δ6.95 (3H, t, J=7 Hz), 7.08 (4H, d, J=7 Hz), 7.20 (4H, t, J=7 Hz), 7.33 to 7.39 (1H, m), 7.45 to 7.50 (2H, m), 7.70 (1H, d, J=9 Hz), 7.80 (1H, d, J=8 Hz), 7.84 (1H, d, J=8 Hz), 7.87 (1H, d, J=8 Hz), 7.97 (1H, d, J=9 Hz), 7.98 (1H, d, J=9 Hz), 8.12 to 8.16 (2H, m), 8.19 (1H, d, J=9 Hz)

Synthesis of Indenopyrene Compound C
(Hereinafter Sometimes Abbreviated as "Compound C")

Intermediate C2 (2.4 g, 4.6 mmoles), dichlorobis(triphenylphosphine)palladium(II) (0.32 g, 0.46 mmoles, 10% Pd) and 1,8-diazabicyclo[5.4.0]-7-undecene (1.0 g, 6.6 mmoles, 1.4 eq.) were dissolved in anhydrous DMF (20 mL) under a nitrogen atmosphere, and the solution was stirred at 140° C. for 11 hours. The reaction mixture was diluted with toluene (200 mL), washed with water (100 mL) and saturated salt water (50 mL) and then dried over anhydrous magnesium sulfate, and the solvent was distilled off. The thus obtained dark brown oil was purified by means of column chromatography (silica gel/hexane and 10% dichloromethane and subsequently, hexane and 17% dichloromethane) to obtain a yellowish orange solid (1.2 g, 59%). This was recrystallized from ethanol (30 mL) and toluene (30 mL) to obtain a yellowish orange tabular crystal (0.9 g).

$^1$H-NMR (400 MHz, CDCl$_3$, TMS): δ6.99 (2H, t, J=7 Hz), 7.12 (4H, d, J=9 Hz), 7.23 (4H, t, J=7 Hz), 7.41 to 7.48 (2H, m), 7.79 (1H, d, J=8 Hz), 7.92 (1H, d, J=9 Hz), 8.01 (1H, d, J=7 Hz), 8.07 (1H, d, J=9 Hz), 8.11 (1H, d, J=7 Hz), 8.13 (1H, d, J=8 Hz), 8.34 (1H, dd, J=8 Hz, 2 Hz), 8.52 (1H, s)

FDMS: Calculated for $C_{34}H_{21}N$=443, found value m/z=443 (M$^+$, 100)

HPLC: 98.6% (UV254, in percent by area)

The thus obtained solid (0.85 g) was subjected to sublimation and purification at 260° C. and $4.7 \times 10^{-4}$ Pa, thereby obtaining a yellow solid (0.80 g).

HPLC: 98.7% (UV254, in percent by area)

Absorption maximum wavelength (CH$_2$Cl$_2$): 451 nm

Fluorescence maximum wavelength (CH$_2$Cl$_2$): 510 nm

Example 1

An ITO transparent electrode-equipped glass substrate of "25 mm×75 mm×0.7 mm in thickness" was ultrasonically cleaned in isopropyl alcohol for 5 minutes and then cleaned with UV ozone for 30 minutes. The transparent electrode line-equipped glass substrate after cleaning was installed in a substrate holder of a vacuum vapor deposition apparatus, and the foregoing Compound A was first subjected to film deposition (film thickness: 30 nm) on the surface on the side on which the transparent electrode line as a lower electrode was formed, at 1 angstrom/sec by means of resistance heating vapor deposition so as to cover the foregoing transparent electrode. Subsequently, fullerene (C$_{60}$) was subjected to film deposition (film thickness: 60 nm) on this film at 1 angstrom/sec by means of resistance heating vapor deposition, and the following Bathocuproin (BCP) was subjected to film deposition (film thickness: 10 nm) thereon at 1 angstrom/sec by means of resistance heating vapor deposition. Finally, metallic Al was continuously subjected to vapor deposition as a counter electrode in a film thickness of 80 nm, thereby forming an organic thin film solar cell. An area was 0.5 cm$^2$.

A performance of the obtained organic thin film solar cell is shown in Table 1.

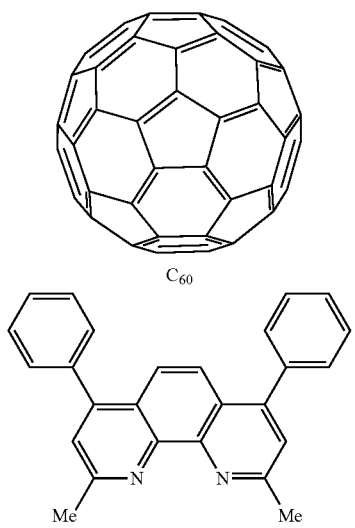

C$_{60}$

BCP

Example 2

An ITO transparent electrode-equipped glass substrate of "25 mm×75 mm×0.7 mm in thickness" was ultrasonically cleaned in isopropyl alcohol for 5 minutes and then cleaned with UV ozone for 30 minutes. The transparent electrode line-equipped glass substrate after cleaning was installed in a substrate holder of a vacuum vapor deposition apparatus, and the foregoing Compound A was first subjected to film deposition (p-layer, film thickness: 5 nm) on the surface on the side on which the transparent electrode line as a lower electrode was formed, at 1 angstrom/sec by means of resistance heating vapor deposition so as to cover the foregoing transparent electrode. Subsequently, Compound A and C$_{60}$ were subjected to vapor co-deposition on this film at 0.2 angstrom/sec and 0.2 angstrom/sec, respectively, thereby forming an i-layer (mixing ratio of p/n=1/1, film thickness: 15 nm). C$_{60}$ was subjected to film deposition (n-layer, film thickness: 45 nm) thereon at 1 angstrom/sec by means of resistance heating vapor deposition, and the following Bathocuproin (BCP) was subjected to film deposition (buffer layer, film thickness: 10 nm) thereon at 1 angstrom/sec by means of resistance heating vapor deposition. Finally, metallic Al was continuously subjected to vapor deposition as a counter electrode in a film thickness of 80 nm, thereby forming an organic thin film solar cell. An area was 0.5 cm$^2$.

A performance of the obtained organic thin film solar cell is shown in Table 1.

Example 3

An organic thin film solar cell was fabricated in the same manner as in Example 2, except that the mixing ratio of the p-compound to the n-compound in the i-layer was changed to p/n=2/1 (the film deposition rates were 0.2 angstrom/sec and 0.1 angstrom/sec, respectively). A performance of the obtained organic thin film solar cell is shown in Table 1.

Example 4

An organic thin film solar cell was fabricated in the same manner as in Example 2, except that the mixing ratio of the p-compound to the n-compound in the i-layer was changed to p/n=1/2 (the film deposition rates were 0.1 angstrom/sec and 0.2 angstrom/sec, respectively). A performance of the obtained organic thin film solar cell is shown in Table 1.

Example 5

An organic thin film solar cell was fabricated in the same manner as in Example 1, except that in Example 1, C$_{60}$ was changed to C$_{70}$. A performance of the obtained organic thin film solar cell is shown in Table 1.

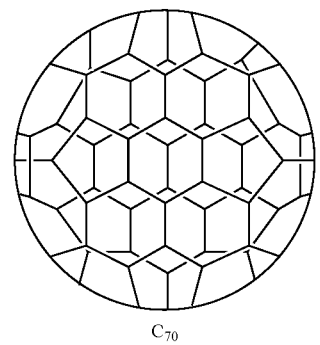

C$_{70}$

Example 6

An organic thin film solar cell was fabricated in the same manner as in Example 3, except that in Example 3, C$_{60}$ was changed to C$_{70}$, the film thickness of the p-layer was changed to 15 nm, the film thickness of the i-layer was changed to 15 nm, and the film thickness of the n-layer was changed to 45 nm. A performance of the obtained organic thin film solar cell is shown in Table 1.

Example 7

An organic thin film solar cell was fabricated in the same manner as in Example 3, except that in Example 3, C$_{60}$ was changed to C$_{70}$, the film thickness of the p-layer was changed to 15 nm, the film thickness of the i-layer was changed to 15 nm, and the film thickness of the n-layer was changed to 60 nm. A performance of the obtained organic thin film solar cell is shown in Table 1.

Example 8

An organic thin film solar cell was fabricated in the same manner as in Example 1, except that in Example 1, Indenopyrene Compound A was changed to Indenopyrene Compound B. A performance of the obtained organic thin film solar cell is shown in Table 1.

Example 9

An organic thin film solar cell was fabricated in the same manner as in Example 5, except that in Example 5, Indenopyrene Compound A was changed to Indenopyrene Compound B. A performance of the obtained organic thin film solar cell is shown in Table 1.

Example 10

An organic thin film solar cell was fabricated in the same manner as in Example 1, except that in Example 1, Indenopyrene Compound A was changed to Indenopyrene Compound C. A performance of the obtained organic thin film solar cell is shown in Table 1.

Comparative Example 1

An organic thin film solar cell was fabricated in the same manner as in Example 1, except that in Example 1, Indenopyrene Compound A was changed to mTPD. A performance of the obtained organic thin film solar cell is shown in Table 1.

Comparative Example 2

An organic thin film solar cell was fabricated in the same manner as in Example 5, except that in Example 5, Indenopyrene Compound A was changed to mTPD. A performance of the obtained organic thin film solar cell is shown in Table 1.

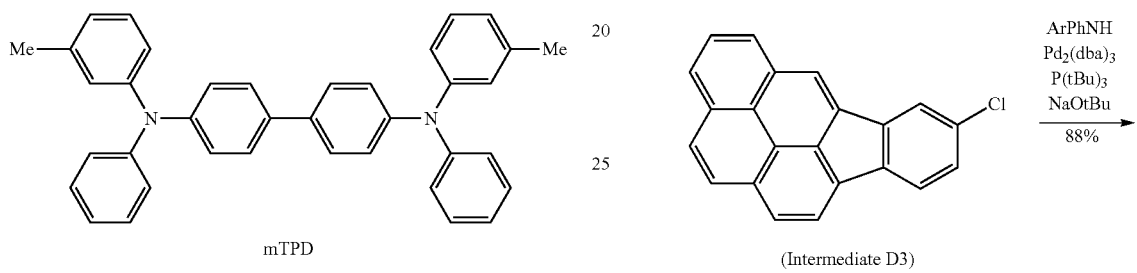

mTPD (Intermediate D2)

(Intermediate D3)

TABLE 1

| | Example | | | | | | | | | | Comparative Example | |
|---|---|---|---|---|---|---|---|---|---|---|---|---|
| | 1 | 2 | 3 | 4 | 5 | 6 | 7 | 8 | 9 | 10 | 1 | 2 |
| p-Layer compound | Compound A | Compound A | Compound A | Compound A | Compound A | Compound A | Compound A | Compound B | Compound B | Compound C | mTPD | mTPD |
| Film thickness (nm) | 30 | 5 | 5 | 5 | 30 | 15 | 15 | 30 | 30 | 30 | 30 | 30 |
| n-Layer compound | $C_{60}$ | $C_{60}$ | $C_{60}$ | $C_{60}$ | $C_{70}$ | $C_{70}$ | $C_{70}$ | $C_{60}$ | $C_{70}$ | $C_{60}$ | $C_{60}$ | $C_{70}$ |
| Film thickness (nm) | 60 | 45 | 45 | 45 | 60 | 45 | 60 | 60 | 60 | 60 | 60 | 60 |
| i-Layer mixing ratio (p/n) | — | 1/1 | 2/1 | 1/2 | — | 2/1 | 2/1 | — | — | — | — | — |
| Film thickness (nm) | 0 | 15 | 15 | 15 | 0 | 15 | 15 | 0 | 0 | 0 | 0 | 0 |
| Voc (V) | 0.93 | 0.98 | 0.96 | 0.95 | 0.93 | 0.96 | 0.96 | 0.98 | 0.98 | 1.01 | 0.71 | 0.85 |
| Jsc (mA/cm$^2$) | 4.01 | 4.43 | 4.39 | 4.25 | 6.64 | 7.92 | 7.48 | 3.65 | 6.57 | 2.94 | 0.71 | 3.93 |
| FF | 0.65 | 0.57 | 0.63 | 0.54 | 0.64 | 0.67 | 0.62 | 0.60 | 0.52 | 0.41 | 0.34 | 0.28 |
| η (%) | 2.40 | 2.46 | 2.65 | 2.17 | 3.99 | 5.08 | 4.41 | 2.16 | 3.34 | 1.22 | 0.17 | 0.92 |

As noted from the comparison with the Comparative Examples, the organic thin film solar cells of the Examples are enhanced in the conversion efficiency and have an excellent solar cell characteristic.

Production Example 4

The following Indenopyrene Compound D was produced through the following synthesis route.

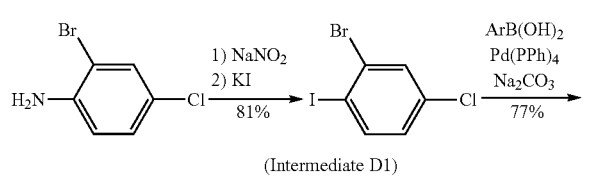

(Intermediate D1)

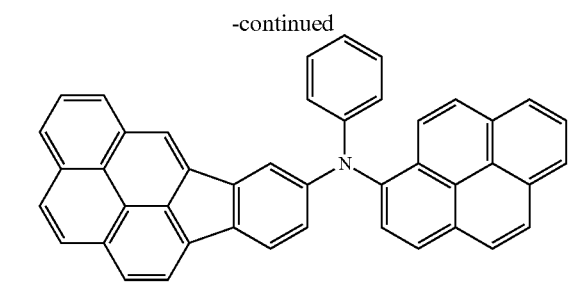

Synthesis of Intermediate D1

2-Bromo-4-chloroaniline (10 g, 48 mmoles) was suspended in hydrochloric acid water (50 mL of concentrated hydrochloric acid and 35 mL of water), and the suspension was cooled on a dry ice/methanol bath at −15° C. A sodium nitrite aqueous solution (3.6 g, 52 mmoles, 1.1 eq./20 mL) was gradually added dropwise thereto over 20 minutes, and the mixture was stirred at from −15° C. to 0° C. for 30 minutes, thereby preparing a diazonium salt. The reaction solution was gradually added dropwise to a potassium iodide aqueous solution (73 g, 0.44 moles, 9 eq./220 mL) at room temperature over 10 minutes. The reaction mixture was stirred at room temperature for 6 hours and then allowed to stand overnight. Dichloromethane (200 mL) was added to the reaction mixture, and subsequently, sodium hydrogensulfite (2 g) was added, thereby deactivating generated iodine. An organic layer was aliquoted, washed with a 10% sodium hydrogensulfite aqueous solution (100 mL) and saturated salt water (30 mL) and dried over anhydrous magnesium sulfate, and the solvent was then distilled off to obtain a red liquid. This was purified by means of column chromatography (silica gel/hexane) to obtain a white needle crystal (12.4 g, 81%).

$^1$H-NMR (400 MHz, CDCl$_3$, TMS): δ6.98 (1H, dd, J=8 Hz, 2 Hz), 7.61 (1H, d, J=2 Hz), 7.74 (1H, d, J=8 Hz)

Synthesis of Intermediate D2

Intermediate D1 (12.4 g, 39 mmoles), 1-pyreneboronic acid (9.6 g, 39 mmoles) and tetrakis(triphenylphosphine)palladium(0) (1.4 g, 1.2 mmoles, 3% Pd) were suspended in 1,2-dimethoxyethane (120 mL) under a nitrogen atmosphere, to which was then added a 2M sodium carbonate aqueous solution (12.4 g, 0.12 moles, 3 eq./60 mL), and the mixture was refluxed for 10 hours. Toluene (200 mL) and water (50 mL) were added to the reaction mixture, an organic layer was aliquoted, washed with saturated salt water (50 mL) and then dried over anhydrous magnesium sulfate, and the solvent was distilled off to obtain a brown solid. This was purified by means of column chromatography (silica gel/hexane and 10% dichloromethane) to obtain a white solid (11.7 g, 77%).

$^1$H-NMR (400 MHz, CDCl$_3$, TMS): δ7.38 (1H, d, J=8 Hz), 7.45 (1H, dd, J=8 Hz, 2 Hz), 7.68 (1H, d, J=9 Hz), 7.81 (1H, d, J=2 Hz), 7.83 (1H, d, J=8 Hz), 7.99 (1H, d, J=7 Hz), 8.00 (1H, d, J=9 Hz), 8.09 (2H, s), 8.16 (1H, d, J=7 Hz), 8.19 (1H, d, J=7 Hz), 8.21 (1H, d, J=8 Hz)

Synthesis of Intermediate D3

Intermediate D2 (11.7 g, 30 mmoles), dichlorobis(triphenylphosphine)palladium(II) (2.1 g, 3 mmoles, 10% Pd) and 1,8-diazabicyclo[5.4.0]-7-undecene (6.4 g, 42 mmoles, 1.4 eq.) were dissolved in anhydrous DMF (120 mL) under a nitrogen atmosphere, and the solution was stirred at 140° C. for 11 hours. The reaction mixture was diluted with methanol (150 mL), and a solid was filtered off to obtain a yellow solid (6.5 g). This was purified by means of column chromatography (silica gel/dichloromethane) to obtain a yellow needle crystal (6.0 g, 64%).

$^1$H-NMR (400 MHz, CDCl$_3$, TMS): δ7.42 (1H, dd, J=9 Hz, 2 Hz), 7.88 (1H, d, J=8 Hz), 8.02 (1H, d, J=2 Hz), 8.05 (1H, d, J=8 Hz), 8.06 (1H, d, J=9 Hz), 8.10 (1H, d, J=9 Hz), 8.19 (1H, d, J=8 Hz), 8.26 (1H, d, J=6 Hz), 8.28 (1H, d, J=7 Hz), 8.38 (1H, d, J=8 Hz), 8.49 (1H, s)

Synthesis of Indenopyrene Compound D
(Hereinafter Sometimes Abbreviated as "Compound D")

Intermediate D3 (1.0 g, 3.2 mmoles), 1-anilinopyrene (1.1 g, 3.8 mmoles, 1.2 eq.), tris (dibenzylideneacetone) dipalladium(0) (0.07 g, 0.076 mmoles, 5% Pd), a tri-t-butylphosphine/toluene solution (66% by weight, 0.04 mL, 0.13 mmoles, 0.8 eq. to Pd) and sodium t-butoxide (0.43 g, 4.5 mmoles, 1.4 eq.) were suspended in anhydrous toluene (50 mL) under a nitrogen atmosphere, and the suspension was refluxed for 11 hours. The reaction mixture was filtered off by passing through a silica gel pad and then washed with toluene (600 mL). A reddish brown solid obtained by distilling off the solvent from the filtrate was purified by means of column chromatography (silica gel/hexane and 33% dichloromethane and subsequently, hexane and 67% dichloromethane) to obtain an orange solid (1.6 g, 88%). This was recrystallized from toluene (60 mL) to obtain an orange tabular crystal (1.1 g).

$^1$H-NMR (400 MHz, CDCl$_3$, TMS): δ7.02 (1H, t, J=7 Hz), 7.17 to 7.21 (2H, m), 7.25 to 7.30 (2H, m), 7.83 (1H, d, J=8 Hz), 7.86 (1H, d, J=7 Hz), 7.94 to 8.02 (5H, m), 8.07 to 8.12 (4H, m), 8.17 to 8.29 (8H, m), 8.34 (1H, s)

FDMS: Calculated for C$_{44}$H$_{25}$N=567, found value m/z=567 (M$^+$, 100)

HPLC: 98.8% (UV254, in percent by area)

A solid (1.1 g) obtained by the foregoing method was subjected to sublimation and purification at 340° C. and 4.0× 10$^{-3}$ Pa, thereby obtaining an orange solid (1.0 g).

HPLC: 98.4% (UV254, in percent by area)

Absorption maximum wavelength (CH$_2$Cl$_2$): 479 nm

Fluorescence maximum wavelength (CH$_2$Cl$_2$): 596 nm

Production Example 5

The following Indenopyrene Compound E was produced through the following synthesis route.

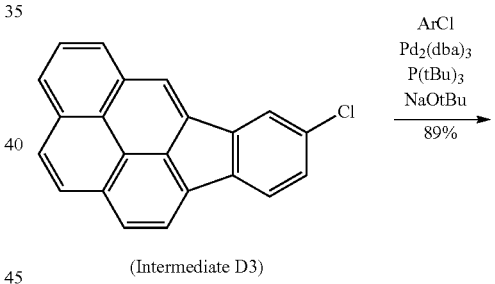

(Intermediate D3)

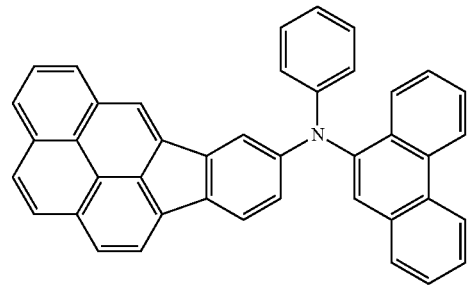

Intermediate D3 (0.96 g, 3.1 mmoles), 9-anilinophenanthrene (1.0 g, 3.7 mmoles, 1.2 eq.), tris(dibenzylideneacetone)dipalladium(0) (0.07 g, 0.076 mmoles, 5% Pd), a tri-t-butylphosphine/toluene solution (66% by weight, 0.04 mL, 0.13 mmoles, 0.8 eq. to Pd) and sodium t-butoxide (0.5 g, 5.2 mmoles, 1.7 eq.) were suspended in anhydrous toluene (50 mL) under a nitrogen atmosphere, and the suspension was refluxed for 11 hours. The reaction mixture was filtered off by passing through a silica gel pad and then washed with toluene (200 mL). A reddish brown solid obtained by distilling off the solvent from the filtrate was purified by means of column chromatography (silica gel/hexane and 33% dichloromethane and subsequently, hexane and 50% dichloromethane) to obtain an orange solid (1.5 g, 89%). This was recrystallized from ethanol (20 mL) and toluene (20 mL) to obtain an orange tabular crystal (1.2 g).

$^1$H-NMR (400 MHz, CDCl$_3$, TMS): δ7.04 (1H, t, J=7 Hz), 7.19 to 7.32 (5H, m), 8.53 (1H, t, J=7 Hz), 7.61 (1H, t, J=7 Hz), 7.68 (2H, t, J=7 Hz), 7.76 (1H, s), 7.82 (1H, d, J=8 Hz), 7.84 (1H, d, J=8 Hz), 7.91 (1H, s), 7.99 (1H, t, J=8 Hz), 8.02 (1H, d, J=8 Hz), 8.10 (1H, d, J=8 Hz), 8.18 to 8.28 (5H, m), 8.38 (1H, s), 8.77 (1H, d, J=8 Hz), 8.80 (1H, d, J=8 Hz)

FDMS: Calculated for C$_{42}$H$_{25}$N=543, found value m/z=543 (M$^+$, 100)

HPLC: 98.8% (UV254, in percent by area)

A solid (1.1 g) obtained by the foregoing method was subjected to sublimation and purification at 340° C. and 5.9× 10$^{-4}$ Pa, thereby obtaining an orange solid (0.92 g).

HPLC: 99.0% (UV254, in percent by area)

Absorption maximum wavelength (CH$_2$Cl$_2$): 475 nm

Fluorescence maximum wavelength (CH$_2$Cl$_2$): 588 nm

Production Example 6

The following Indenopyrene Compound F was produced through the following synthesis route.

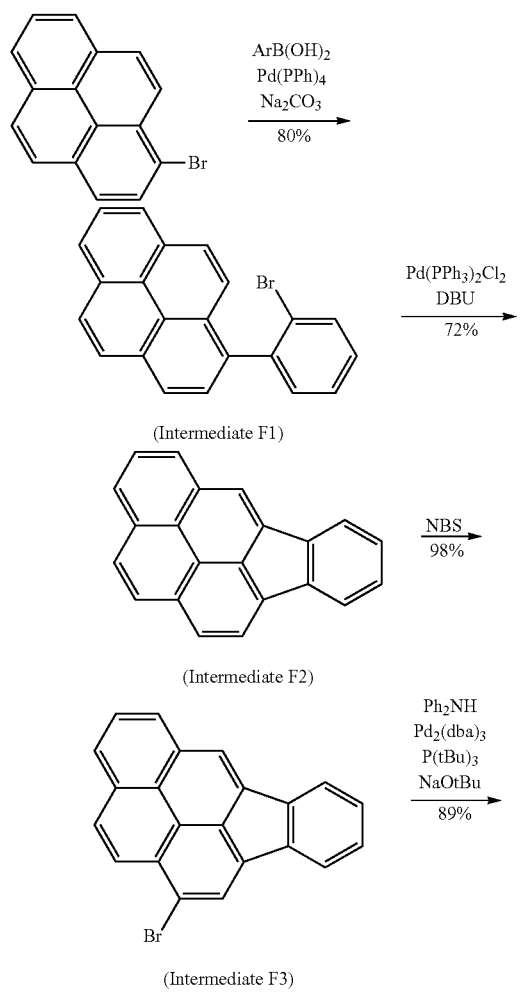

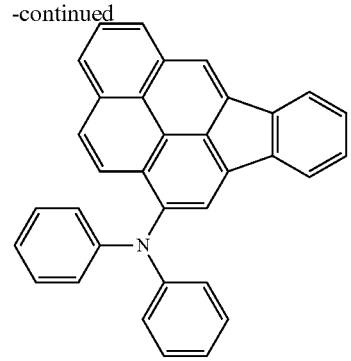

Synthesis of Intermediate F1

2-Bromophenylboronic acid (6.9 g, 34 mmoles, 1.2 eq.), 1-bromopyrene (8.0 g, 28 mmoles) and tetrakis(triphenylphosphine)palladium(0) (0.65 g, 0.56 mmoles, 2% Pd) were suspended in 1,2-dimethoxyethane (100 mL) under a nitrogen atmosphere, to which was then added a 2M sodium carbonate aqueous solution (11 g, 0.10 moles, 3 eq./50 mL), and the mixture was refluxed for 10 hours. Toluene (200 mL) and water (50 mL) were added to the reaction mixture, an organic layer was aliquoted, washed with saturated salt water (50 mL) and then dried over anhydrous magnesium sulfate, and the solvent was distilled off to obtain a yellow oil. This was purified by means of column chromatography (silica gel/hexane and 10% dichloromethane) to obtain a white tabular crystal (8.0 g, 80%).

$^1$H-NMR (400 MHz, CDCl$_3$, TMS): δ7.32 to 7.36 (1H, m), 7.46 (2H, d, J=4 Hz), 7.72 (1H, d, J=9 Hz), 7.79 (1H, d, J=8 Hz), 7.89 (1H, d, J=8 Hz), 7.98 (1H, d, J=8 Hz), 8.00 (1H, d, J=9 Hz), 8.09 (2H, s), 8.15 (1H, d, J=8 Hz), 8.19 (1H, d, J=8 Hz), 8.22 (1H, d, J=8 Hz)

Synthesis of Intermediate F2

Intermediate F1 (8.0 g, 22 mmoles), dichlorobis(triphenylphosphine)palladium(II) (1.6 g, 2.3 mmoles, 10% Pd) and 1,8-diazabicyclo[5.4.0]-7-undecene (4.7 g, 31 mmoles, 1.4 eq.) were dissolved in anhydrous DMF (90 mL) under a nitrogen atmosphere, and the solution was stirred at 140° C. for 11 hours. The reaction mixture was diluted with toluene (200 mL), washed with water (100 mL) and saturated salt water (50 mL) and then dried over anhydrous magnesium sulfate, and the solvent was distilled off to obtain a yellow solid. This was purified by means of column chromatography (silica gel/hexane and 17% dichloromethane and subsequently, hexane and 33% dichloromethane) to obtain a yellow solid (4.4 g, 72%).

$^1$H-NMR (400 MHz, CDCl$_3$, TMS): δ7.39 (1H, t, J=7 Hz), 7.44 (1H, t, J=7 Hz), 7.98 (2H, t, J=8 Hz), 8.20 (1H, d, J=9 Hz), 8.05 (2H, d, J=8 Hz), 8.14 (1H, d, J=8 Hz), 8.19 (1H, d, J=8 Hz), 8.28 (1H, d, J=8 Hz), 8.31 (1H, d, J=8 Hz), 8.45 (1H, s)

Synthesis of Intermediate F3

Intermediate F2 (4.4 g, 16 mmoles) was suspended in anhydrous DMF (75 mL), to which was then added an anhydrous DMF solution (5 mL) of N-bromosuccinimide (3.1 g, 17 mmoles, 1.1 eq.), and the mixture was stirred at 45° C. for 8 hours. The reaction mixture was cooled on a water bath and then diluted with water (100 mL), and a formed solid was filtered off and then washed with water and methanol to obtain a yellow solid (5.6 g, 98%).

$^1$H-NMR (400 MHz, CDCl$_3$, TMS): δ7.44 (1H, t, J=7 Hz, 2 Hz), 7.47 (1H, t, J=7 Hz, 2 Hz), 7.92 (1H, dd, J=6 Hz, 1 Hz), 8.02 (1H, d, J=8 Hz), 8.04 (1H, dd, J=6 Hz, 1 Hz), 8.09 (1H, d, J=9 Hz), 8.24 (1H, d, J=8 Hz), 8.29 (1H, d, J=9 Hz), 8.34 (1H, d, J=8 Hz), 8.42 (1H, s), 8.47 (1H, s)

Synthesis of Indenopyrene Compound F (Hereinafter Sometimes Abbreviated as "Compound F")

Intermediate F3 (2.0 g, 5.6 mmoles), diphenylamine (1.1 g, 6.5 mmoles, 1.2 eq.), tris(dibenzylideneacetone)dipalladium (0) (0.13 g, 0.14 mmoles, 5% Pd), a tri-t-butylphosphine/toluene solution (66% by weight, 0.07 mL, 0.23 mmoles, 0.8 eq. to Pd) and sodium t-butoxide (0.8 g, 8.3 mmoles, 1.5 eq.) were suspended in anhydrous toluene (50 mL) under a nitrogen atmosphere, and the suspension was refluxed for 11 hours. The reaction mixture was filtered off by passing through a silica gel pad and then washed with toluene (400 mL). A reddish brown solid (2.5 g) obtained by distilling off the solvent from the filtrate was recrystallized from toluene (40 mL) to obtain an orange tabular crystal (2.2 g, 89%).

$^1$H-NMR (400 MHz, CDCl$_3$, TMS): δ6.96 (2H, t, J=7 Hz), 7.15 (4H, d, J=7 Hz), 7.22 (4H, t, J=7 Hz), 7.41 to 7.43 (2H, m), 7.89 to 7.91 (2H, m), 7.99 to 8.06 (2H, m), 8.10 to 8.13 (1H, m), 8.17 (1H, d, J=8 Hz), 8.22 (1H, s), 8.39 (1H, d, J=8 Hz), 8.55 (1H, s)

FDMS: Calculated for C$_{34}$H$_{21}$N=443, found value m/z=443 (M$^+$, 100)

HPLC: 99.7% (UV254, in percent by area)

A solid (1.15 g) obtained by the foregoing method was subjected to sublimation and purification at 280° C. and 1.6× 10$^{-4}$ Pa, thereby obtaining an orange solid (1.11 g).

HPLC: 99.7% (UV254, in percent by area)

Absorption maximum wavelength (CH$_2$Cl$_2$): 461 nm

Fluorescence maximum wavelength (CH$_2$Cl$_2$): 547 nm

Production Example 7

The following Indenopyrene Compound G was produced through the following synthesis route.

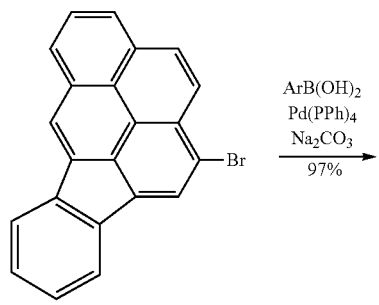

(Intermediate F3)

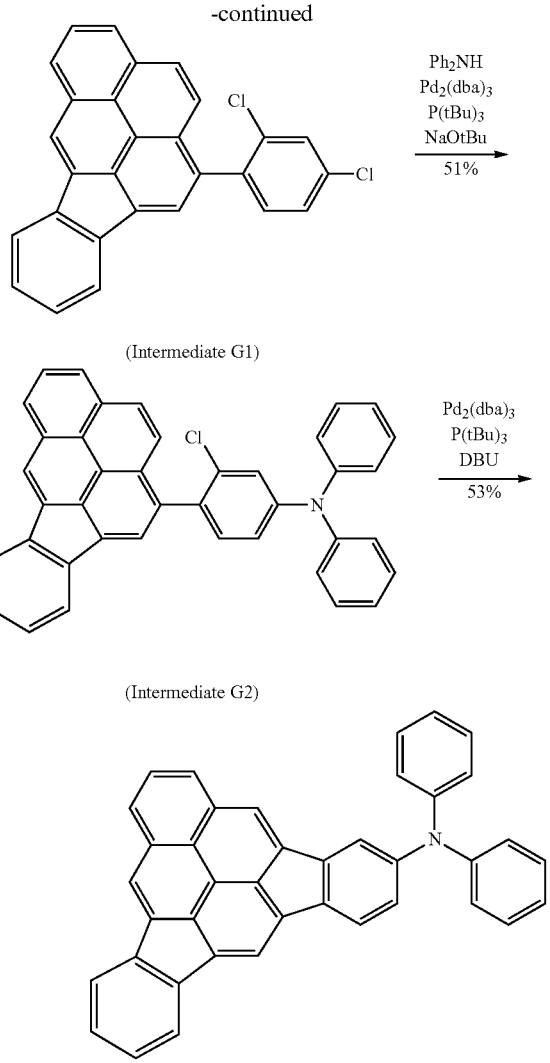

Synthesis of Intermediate G1

2,4-Dichlorophenylboronic acid (1.4 g, 7.3 mmoles, 1.2 eq.), Intermediate F3 (2.1 g, 5.9 mmoles) and tetrakis(triphenylphosphine)palladium(0) (0.2 g, 0.17 mmoles, 3% Pd) were suspended in 1,2-dimethoxyethane (45 mL) under a nitrogen atmosphere, to which was then added a 2M sodium carbonate aqueous solution (2.3 g, 22 mmoles, 3 eq./12 mL), and the mixture was refluxed for 10 hours. The reaction mixture was diluted with water (100 mL), and a solid was filtered off and then washed with methanol to obtain a brown solid (2.8 g). This was purified by means of column chromatography (silica gel/hexane and 33% dichloromethane) to obtain a yellow solid (2.4 g, 97%).

$^1$H-NMR (400 MHz, CDCl$_3$, TMS): δ7.39 to 7.48 (4H, m), 7.67 (1H, d, J=2 Hz), 7.71 (1H, d, J=9 Hz), 7.96 to 8.02 (3H, m), 8.09 (1H, d, J=7 Hz), 8.20 (1H, d, J=7 Hz), 8.23 (1H, s), 8.36 (1H, d, J=8 Hz), 8.53 (1H, s)

Synthesis of Intermediate G2

Intermediate G1 (2.4 g, 5.7 mmoles), diphenylamine (1.1 g, 6.5 mmoles, 1.1 eq.), tris(dibenzylideneacetone)dipalladium(0) (0.13 g, 0.14 mmoles, 5% Pd), a tri-t-butylphosphine/toluene solution (66% by weight, 0.07 mL, 0.23 mmoles, 0.8 eq. to Pd) and sodium t-butoxide (0.8 g, 8.3 mmoles, 1.5 eq.) were dissolved in anhydrous toluene (30 mL) under a nitrogen atmosphere, and the solution was refluxed for 11 hours. The reaction mixture was filtered off by passing through a silica gel pad and then washed with toluene (200 mL). A red oil obtained by distilling off the solvent from the filtrate was purified by means of column chromatography (silica gel/hexane and 17% dichloromethane) to obtain a pale brown solid (1.6 g, 510).

$^1$H-NMR (400 MHz, CDCl$_3$, TMS): δ7.10 to 7.14 (3H, m), 7.24 to 7.59 (12H, m), 7.90 (1H, d, J=9 Hz), 7.99 to 8.05 (3H, m), 8.12 (1H, d, J=6 Hz), 8.24 (1H, d, J=8 Hz), 8.33 (1H, s), 8.40 (1H, d, J=7 Hz), 8.57 (1H, s)

Synthesis of Indenopyrene Compound G (Hereinafter Sometimes Abbreviated as "Compound G")

Intermediate G2 (1.6 g, 2.9 mmoles), 1,8-diazabicyclo[5.4.0]-7-undecene (0.7 g, 4.6 mmoles, 1.5 eq.), tris(dibenzylideneacetone)dipalladium(0) (0.13 g, 0.14 mmoles, 10% Pd) and a tri-t-butylphosphine/toluene solution (66% by weight, 0.13 mL, 0.42 mmoles, 1.5 eq. to Pd) were dissolved in anhydrous DMF (10 mL) under a nitrogen atmosphere, and the solution was stirred at 140° C. for 10 hours. The reaction mixture was diluted with methanol (70 mL), and a solid was filtered off to obtain a reddish brown solid (1.2 g). This was dissolved in hot toluene (400 mL) and filtered off, thereby removing palladium black. The filtrate was concentrated to obtain a reddish brown solid (0.8 g, 53%).

$^1$H-NMR (400 MHz, CDCl$_3$, TMS): δ7.08 (2H, t, J=7 Hz), 7.18 to 7.35 (9H, m), 7.44 (1H, t, J=7 Hz), 7.51 (1H, t, J=7 Hz), 7.89 (1H, d, J=2 Hz), 7.95 (1H, d, J=8 Hz), 8.05 (1H, d, J=8 Hz), 8.09 (1H, d, J=8 Hz), 8.13 (1H, d, J=7 Hz), 8.40 (2H, t, J=4 Hz), 8.46 (1H, d, J=8 Hz), 8.50 (1H, s), 8.57 (1H, s)

FDMS: Calculated for C$_{40}$H$_{23}$N=517, found value m/z=517 (M$^+$, 100)

HPLC: 98.2% (UV254, in percent by area)

A solid (0.79 g) obtained by the foregoing method was subjected to sublimation and purification at 320° C. and 3.3× 10$^{-4}$ Pa, thereby obtaining a red solid (0.71 g).

HPLC: 98.5% (UV254, in percent by area)

Absorption maximum wavelength (CH$_2$Cl$_2$): 513 nm

Fluorescence maximum wavelength (CH$_2$Cl$_2$): 548 nm

Production Example 8

The following Indenopyrene Compound H was produced through the following synthesis route.

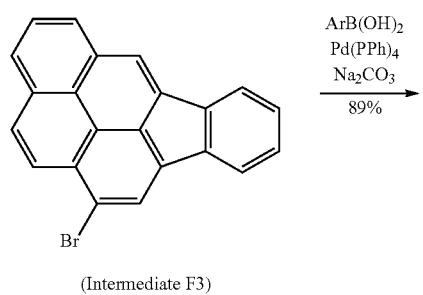

(Intermediate F3)

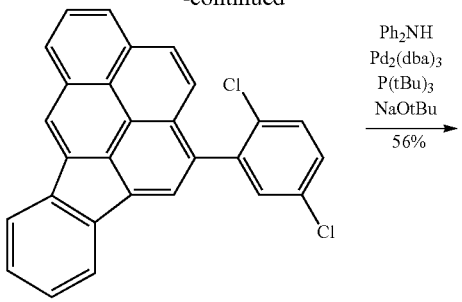

(Intermediate H1)

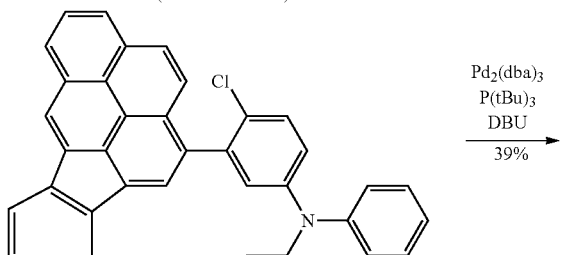

(Intermediate H2)

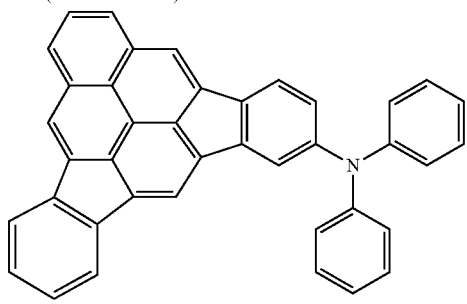

Synthesis of Intermediate H1

2,5-Dichlorophenylboronic acid (2.6 g, 14 mmoles, 1.2 eq.), Intermediate F3 (4.0 g, 11 mmoles) and tetrakis(triphenylphosphine)palladium(0) (0.38 g, 0.33 mmoles, 3% Pd) were suspended in 1,2-dimethoxyethane (90 mL) under a nitrogen atmosphere, to which was then added a 2M sodium carbonate aqueous solution (4.5 g, 42 mmoles, 3 eq./20 mL), and the mixture was refluxed for 10 hours. Toluene (200 mL) and water (50 mL) were added to the reaction mixture, an organic layer was aliquoted, and the organic layer was washed with saturated salt water (50 mL) and then dried over anhydrous magnesium sulfate, followed by distilling off the solvent to obtain a yellow oil. This was purified by means of column chromatography (silica gel/hexane and 17% dichloromethane) to obtain a yellow solid (4.1 g, 890).

$^1$H-NMR (400 MHz, CDCl$_3$, TMS): δ7.41 to 7.48 (3H, m), 7.55 to 7.58 (2H, m), 7.73 (1H, d, J=9 Hz), 7.98 (1H, d, J=6 Hz), 8.03 (2H, t, J=8 Hz), 8.11 (1H, d, J=6 Hz), 8.23 (1H, d, J=8 Hz), 8.25 (1H, s), 8.39 (1H, d, J=8 Hz), 8.55 (1H, s)

Synthesis of Intermediate H2

Intermediate H1 (4.1 g, 9.7 mmoles), diphenylamine (2.0 g, 12 mmoles, 1.1 eq.), tris(dibenzylideneacetone)dipalladium(0) (0.13 g, 0.14 mmoles, 5% Pd), a tri-t-butylphosphine/toluene solution (66% by weight, 0.07 mL, 0.23 mmoles, 0.8 eq. to Pd) and sodium t-butoxide (1.3 g, 14 mmoles, 1.4 eq.) were suspended in anhydrous toluene (30 mL) under a nitrogen atmosphere, and the suspension was refluxed for 11 hours. The reaction mixture was filtered off by passing through a silica gel pad and then washed with toluene (200 mL). A red oil obtained by distilling off the solvent from the filtrate was purified by means of column chromatography (silica gel/hexane and 33% dichloromethane) to obtain an orange solid (3.0 g, 56%).

$^1$H-NMR (400 MHz, CDCl$_3$, TMS): δ7.01 (2H, t, J=7 Hz), 7.15 to 7.29 (10H, m), 7.39 to 7.45 (2H, m), 7.47 (1H, d, J=9 Hz), 7.83 (1H, d, J=9 Hz), 7.97 to 8.03 (3H, m), 8.09 (1H, d, J=6 Hz), 8.21 (1H, d, J=8 Hz), 8.27 (1H, s), 8.37 (1H, d, J=8 Hz), 8.53 (1H, s)

Synthesis of Indenopyrene Compound H
(Hereinafter Sometimes Abbreviated as "Compound H")

Intermediate H2 (3.0 g, 2.9 mmoles), 1,8-diazabicyclo[5.4.0]-7-undecene (1.2 g, 7.9 mmoles, 1.5 eq.), tris(dibenzylideneacetone)dipalladium(0) (0.25 g, 0.27 mmoles, 10% Pd) and a tri-t-butylphosphine/toluene solution (66% by weight, 0.25 mL, 0.82 mmoles, 1.5 eq. to Pd) were suspended in anhydrous DMF (20 mL) under a nitrogen atmosphere, and the suspension was stirred at 140° C. for 10 hours. The reaction mixture was diluted with toluene (100 mL), and a solid was filtered off to obtain a reddish brown solid (1.5 g). This was recrystallized from toluene (120 mL) to obtain a red solid (1.1 g, 39%).

$^1$H-NMR (400 MHz, CDCl$_3$, TMS): δ7.10 to 7.18 (4H, m), 7.29 (4H, d, J=7 Hz), 7.36 (4H, t, J=7 Hz), 7.39 (1H, t, J=7 Hz), 7.50 (1H, t, J=7 Hz), 7.76 (1H, d, J=2 Hz), 7.90 (2H, d, J=8 Hz), 7.99 (1H, t, J=8 Hz), 8.01 (1H, d, J=7 Hz), 8.15 (1H, s), 8.18 (1H, s), 8.22 (1H, s), 8.29 (1H, dd, J=8 Hz, 2 Hz)

FDMS: Calculated for $C_{40}H_{23}N$=517, found value m/z=517 (M$^+$, 100)

HPLC: 98.2% (UV254, in percent by area)

A solid (1.1 g) obtained by the foregoing method was subjected to sublimation and purification at 320° C. and 6.3× 10$^{-4}$ Pa, thereby obtaining an orange solid (0.9 g).

HPLC: 98.4% (UV254, in percent by area)

Absorption maximum wavelength (CH$_2$Cl$_2$): 453 nm

Fluorescence maximum wavelength (CH$_2$Cl$_2$): 614 nm

Example 11

An organic thin film solar cell was fabricated in the same manner as in Example 1, except that in Example 1, Indenopyrene Compound A was changed to Indenopyrene Compound D. A performance of the obtained organic thin film solar cell is shown in Table 2.

Example 12

An organic thin film solar cell was fabricated in the same manner as in Example 1, except that in Example 1, Indenopyrene Compound A was changed to Indenopyrene Compound E. A performance of the obtained organic thin film solar cell is shown in Table 2.

Example 13

An organic thin film solar cell was fabricated in the same manner as in Example 1, except that in Example 1, Indenopyrene Compound A was changed to Indenopyrene Compound F. A performance of the obtained organic thin film solar cell is shown in Table 2.

Example 14

An organic thin film solar cell was fabricated in the same manner as in Example 1, except that in Example 1, Indenopyrene Compound A was changed to Indenopyrene Compound G. A performance of the obtained organic thin film solar cell is shown in Table 2.

Example 15

An organic thin film solar cell was fabricated in the same manner as in Example 1, except that in Example 1, Indenopyrene Compound A was changed to Indenopyrene Compound H. A performance of the obtained organic thin film solar cell is shown in Table 2.

TABLE 2

| | Example | | | | |
|---|---|---|---|---|---|
| | 11 | 12 | 13 | 14 | 15 |
| p-Layer compound | Compound D | Compound E | Compound F | Compound G | Compound H |
| Film thickness (nm) | 30 | 30 | 30 | 30 | 30 |
| n-Layer compound | $C_{60}$ | $C_{60}$ | $C_{60}$ | $C_{60}$ | $C_{60}$ |
| Film thickness (nm) | 60 | 60 | 60 | 60 | 60 |
| i-Layer mixing ratio (p/n) | — | — | — | — | — |
| Film thickness (nm) | 0 | 0 | 0 | 0 | 0 |
| Voc (V) | 0.98 | 0.94 | 0.93 | 0.90 | 0.97 |
| Jsc (mA/cm$^2$) | 3.84 | 3.63 | 3.56 | 3.87 | 3.65 |
| FF | 0.65 | 0.61 | 0.59 | 0.55 | 0.62 |
| η (%) | 2.43 | 2.07 | 1.94 | 1.91 | 2.19 |

As noted from the comparison with the Comparative Examples, the organic thin film solar cells of the Examples are enhanced in the conversion efficiency and have an excellent solar cell characteristic.

INDUSTRIAL APPLICABILITY

The indenopyrene compound of the present invention can be utilized for organic electronics materials, for example, organic electroluminescence materials, organic semiconductor materials, organic field effect transistor materials, organic solar cell materials, etc.

The invention claimed is:

1. An indenopyrene compound represented by the following general formula (I):

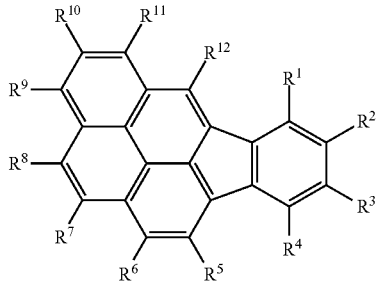

(I)

wherein
each of $R^1$ to $R^{12}$ independently represents a hydrogen atom or a group selected among a substituted or unsubstituted alkyl group having a carbon number of from 1 to 40, a substituted or unsubstituted aryl group having a carbon number of from 6 to 40, a substituted or unsubstituted heteroaryl group having a carbon number of from 3 to 40, a substituted or unsubstituted alkoxy group having a carbon number of from 1 to 40, a substituted or unsubstituted aryloxy group having a carbon number of from 6 to 40 and a disubstituted amino group substituted with a group having a carbon number of from 1 to 40;
$R^6$ and $R^7$ may be bonded to each other to form a ring; and
at least one member of $R^2$, $R^3$, $R^6$ and $R^9$ is a disubstituted amino group substituted with a group having a carbon number of from 1 to 40;
wherein the disubstituted amino group substituted with a group having a carbon number of from 1 to 40 is an amino group represented by the general formula (II):

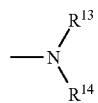

(II)

wherein
each of $R^{13}$ and $R^{14}$ independently represents a substituted or unsubstituted aryl group having a carbon number of from 6 to 40.

2. The indenopyrene compound according to claim 1, wherein in the general formula (I), each of $R^1$ to $R^{12}$ other than a disubstituted amino group substituted with a group having a carbon number of from 1 to 40 is independently a hydrogen atom, a substituted or unsubstituted alkyl group having a carbon number of from 1 to 40 or a substituted or unsubstituted aryl group having a carbon number of from 6 to 40.

3. The indenopyrene compound according to claim 1, wherein in the general formula (I), $R^1$ to $R^{12}$ other than a disubstituted amino group substituted with a group having a carbon number of from 1 to 40 are a hydrogen atom.

4. An organic thin film solar cell material comprising
the indenopyrene compound represented by the following general formula (I):

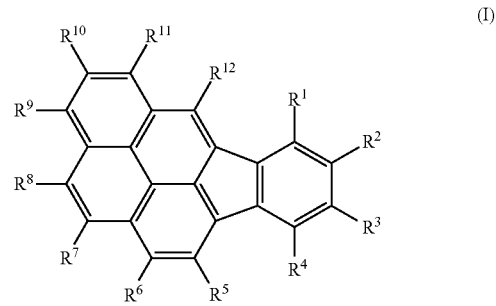

(I)

wherein
each of $R^1$ to $R^{12}$ independently represents a hydrogen atom or a group selected among a substituted or unsubstituted alkyl group having a carbon number of from 1 to 40, a substituted or unsubstituted aryl group having a carbon number of from 6 to 40, a substituted or unsubstituted heteroaryl group having a carbon number of from 3 to 40, a substituted or unsubstituted alkoxy group having a carbon number of from 1 to 40, a substituted or unsubstituted aryloxy group having a carbon number of from 6 to 40 and a disubstituted amino group substituted with a group having a carbon number of from 1 to 40;
$R^6$ and $R^7$ may be bonded to each other to form a ring; and
at least one member of $R^2$, $R^3$, $R^6$, and $R^9$ is a disubstituted amino group substituted with a group having a carbon number of from 1 to 40;
wherein the disubstituted amino group substituted with a group having a carbon number of from 1 to 40 is an amino group represented by the general formula (II):

(II)

wherein
each of $R^{13}$ and $R^{14}$ independently represents a substituted or unsubstituted aryl group having a carbon number of from 6 to 40;
and at least one further compound suitable for an organic thin film solar cell material.

5. An organic thin film solar cell material according to claim 4, wherein in the compound of formula I, each of $R^1$ to $R^{12}$ other than a disubstituted amino group substituted with a group having a carbon number of from 1 to 40 is independently a hydrogen atom, a substituted or unsubstituted alkyl group having a carbon number of from 1 to 40 or a substituted or unsubstituted aryl group having a carbon number of from 6 to 40.

6. An organic thin film solar cell material according to claim 4, wherein in the compound of formula I, $R^1$ to $R^{12}$ other than a disubstituted amino group substituted with a group having a carbon number of from 1 to 40 are a hydrogen atom.

7. An organic thin film solar cell having at least a p-layer (hole transport layer) between a pair of electrodes, wherein the p-layer contains the organic thin film solar cell material according to claim 4.

8. An organic thin film solar cell having at least a p-layer (hole transport layer) between a pair of electrodes, wherein the p-layer contains the organic thin film solar cell material according to claim 6.

9. An apparatus comprising the organic thin film solar cell having at least a p-layer (hole transport layer) between a pair of electrodes, wherein the p-layer contains the organic thin film solar cell material according to claim 4.

* * * * *

UNITED STATES PATENT AND TRADEMARK OFFICE
CERTIFICATE OF CORRECTION

| | |
|---|---|
| PATENT NO. | : 8,759,590 B2 |
| APPLICATION NO. | : 13/056777 |
| DATED | : June 24, 2014 |
| INVENTOR(S) | : Hidetsugu Ikeda et al. |

It is certified that error appears in the above-identified patent and that said Letters Patent is hereby corrected as shown below:

ON THE TITLE PAGE:

Item (22) reads:

(22) PCT Filed: Oct. 4, 2009

Should read:

(22) PCT Filed: April 10, 2009

Signed and Sealed this
Twenty-first Day of October, 2014

Michelle K. Lee
*Deputy Director of the United States Patent and Trademark Office*